United States Patent [19]

Segall et al.

[11] Patent Number: 5,723,281
[45] Date of Patent: Mar. 3, 1998

[54] PLASMA-LIKE SUBSTANCE

[75] Inventors: Paul E. Segall; Harold D. Waitz; Hal Sternberg; Judith M. Segall, all of Berkeley, Calif.

[73] Assignee: BioTime, Inc., Berkeley, Calif.

[21] Appl. No.: 471,396

[22] Filed: Jun. 6, 1995

Related U.S. Application Data

[60] Division of Ser. No. 133,527, Oct. 7, 1993, abandoned, which is a continuation-in-part of Ser. No. 71,533, Jun. 4, 1993, Pat. No. 5,407,428.

[51] Int. Cl.$^6$ .............. A01N 1/00; A61K 31/715; A61K 31/72; A61K 47/36
[52] U.S. Cl. .............. 435/1.2; 435/1.1; 435/1.3; 514/54; 514/59; 514/60; 424/717
[58] Field of Search .............. 435/1.1, 1.2, 1.3; 514/54, 59, 60; 424/717

[56] References Cited

U.S. PATENT DOCUMENTS

| | | |
|---|---|---|
| 3,356,570 | 12/1967 | Butcher. |
| 3,758,382 | 9/1973 | Knorpp. |
| 4,663,166 | 5/1987 | Veech. |
| 4,923,442 | 5/1990 | Segall et al. .............. 604/52 |
| 5,130,230 | 7/1992 | Segall et al. . |

OTHER PUBLICATIONS

Belzer et al., "Combination Perfusion–Cold Storage for Optimum Cadaver Kidney Function and Utilization" *Transplantation* (1985) 39(2):118–121.

Bishop et al., "Evaluation of Hypertonic Citrate Flushing Solution for Kidney Preservation Using the Isolated Perfused Rat Kidney" *Transplantation* (1978) 25(5):235–239.

Carpenter et al., *J. Dairy Sci.* (1990) 73:3627–3636.

*Clinical Diagnosis by Laboratory Methods*, 15th Ed., (1974), Davidsohn et al (eds.) Appendix 3, pp. 1376–1382.

Collins, "Hypothermic Kidney Storage" *Transplant Proc.* (1977) 9(3):1529–1534.

Fischer et al. "Flush Solution 2, A New Concept for One-to-Three Day Hypothermic Renal Storage Preservation" *Transplantation* (1985) 39(2):122–126.

Kallerhoff et al., "Effects of Preservation Conditions and Temperature on Tissue Acidification in Canine Kidneys" *Transplantation* (1985) 39(5):485–489.

Ross et al. "72–HR Canine Kidney Preservation Without Continuous Perfusion" *Transplantation* (1976) 21(6):498–501.

Sprung et al., "Effects of Acute Hypothermia and b–Adrenergic Receptor Blockade on Serum Potassium Concentration in Rats" *Critical Care Medicine* (1991), 19(12):1545–51.

Wall et al., "Simple Hypothermic Preservation for Transporting Human Livers Long Distances for Transplantation" *Transplantation* (1977) 23(3):210–216.

*Primary Examiner*—Leon B. Lankford, Jr.
*Assistant Examiner*—Francisco C. Prats
*Attorney, Agent, or Firm*—Karl Bozicevic; Bozicevic & Reed, LLP; Bret Field

[57] ABSTRACT

An artificial plasma-like substance having at least one water soluble polysaccharide oncotic agent selected from the group consisting of high molecular weight hydroxyethyl starch, low molecular weight hydroxyethyl starch, dextran 40 and dextran 70, and albumin which is buffered by lactate and has a pre-administration pH of between 5 and 6.5 is disclosed. Also disclosed is an artificial plasma-like solution having at least two water soluble polysaccharide oncotic agents one of which is eliminated from the circulation slowly and the other of which is eliminated from the circulation quickly. Supplimentation of the plasma-like solution with certain ions is described. A system for administration of the plasma-like solution to a subject wherein the system comprises a first and second solution each having particular buffers is described. The plasma-like solution including cryoprotective adducts is also disclosed. The use of the plasma-like solution in organ transplant, novel chemotherapy procedures, and tissue, organ and organism cryopreservation are also disclosed.

11 Claims, No Drawings

PLASMA-LIKE SUBSTANCE

CROSS-REFERENCES

This application is a divisional of our application Ser. No. 08/133,527, filed Oct. 7, 1993, now abandoned, which is a continuation-in-part application Ser. No. 08/071,533, filed Jun. 4, 1993, now U.S. Pat. No. 5,407,428, to which we claim priority under 35 USC § 120 and which are incorporated herein by reference in their entirety.

FIELD OF THE INVENTION

The invention relates to the field of plasma-like solutions which may be used to treat hypovolemic subjects or to substitute for the blood or plasma of a subject.

BACKGROUND

Perfusion solutions and blood substitutes are known. The blood substitutes of Collins et al, Kidney preservation for transplantation. Lancet 1219–1222 (1969); Collins G. M., Hypothermic kidney storage. Transplant. Proc. I:1529 (1977); Filcher et al, Flush solution 2, a new concept for one to three day hypothermic renal storage preservation. Transplantation 39:2, 122–126 (1985); Robs et al, 72-hour canine kidney preservation without continuous perfusion. Transplantation 21:498 (1976); Sacks et al, Transplantation 19:283 (1974) and Kallerhoff et al, Effects of the preservation conditions and temperature on tissue acidification in canine kidneys. Transplantation 39:5, 485–489 (1985) all consist only of low molecular weight molecules that readily traverse the capillary bed of the subject and thus are generally incapable of maintaining proper ionic or fluid balance or plasma volume when used in an intact mammalian subject.

Klebanoff and Phillips, Cryobiology 6:121–125 (1969) disclosed hypothermic asanguinous perfusion of dogs with 11 of 15 subjects surviving up to 95 minutes when perfused with buffered Ringer's lactate at 7.1 to 16 degrees C. (44.8–60.8 degrees F.). Those blood substitutes that have an impermeable substance to maintain volume use human serum albumin or a mixture of plasma proteins, as the impermeate molecule to maintain blood volume. These are disclosed in Wall et al., Simple hypothermic preservation for transporting human livers long distances for transplantation, Transplantation, 23:210 (1977); Belzer et al., Combination perfusion-cold storage for optimum cadaver kidney function and utilization, Transplantation 39:2, 118–121, (1985).

Haff et al., Journal of Surgical Research 19:1, 13–19 (1975) describe the asanguineous hypothermic perfusion of dogs using two solutions: the first, a flush solution comprised of pooled delipidated homologous plasma and electrolytes, and the second comprised of pooled delipidated homologous plasma, electrolytes and additional potassium chloride at a concentration of 10 milliEquivalents/liter (mEq/1). Haff et al also disclose the use of a pulsatile pump oxygenator and hypothermic perfusion with their solutions and suggest that the procedures could be used for long distance transport of cadaver organ donors and as an alternative to hypothermic circulatory arrest for blood-free intricate surgery.

Non plasma-based solutions for organ preservation are disclosed in Bishop et al., Evaluation of hypertonic citrate flushing solution for kidney preservation using the isolated perfused rat kidney. Transplantation 25:5, 235–239 (1978). This article discloses a perfusion solution that included 50 g/liter dextran 40, a concentration that differs markedly from those of the solutions of the present invention. In addition, the electrolyte and ion concentrations differ markedly from those disclosed for the present invention.

Segall et al., Federation Proceedings 44(3):623, (1985) disclose that a Ringer's lactate-based heparinized blood substitute containing 6% dextran 40 was used to lower the body temperature of hamsters prior to the circulation of cold-protective solutions, which are not disclosed, for 1 to 1.5 hours.

Segall et al., (1987) Federation Proceedings, page 1338, disclose that a blood substitute, which included dextrose (180 mg/dl) and 25 mM HEPES, was used to perfuse a dog to 3 degrees C. when perfusion was stopped entirely. There is no disclosure of the complete composition of the blood substitute.

Segall et al, U.S. Pat. No. 4,923,442 and the reissue thereof disclose a number of solutions used in blood substitution of living subjects all of which include at least some concentration of a cardioplegia agent, usually potassium ion. Segall et al., U.S. Pat. No. 4,923,442 also discloses surgical methods, particularly in respect to instrument placement and the control of pulmonary wedge pressure generally applicable to perfusion of subjects. U.S. Pat. No. 4,923,442 and its reissue are incorporated herein by reference.

Segall et al., U.S. Pat. No. 5,130,230 discloses a blood substitute which may be used as a system of solutions in which a number of solutions, in some embodiments two solutions and in other embodiments four solutions, are used sequentially to completely replace the blood of living subjects. In one of the embodiments, one of the solutions, identified as the recovery solution, of a four solution system is disclosed as having, in addition to several dissolved salts and other constituents, dissolved potassium chloride in a concentration range of 0 to 10 mM. In describing the blood substitute, the specification of U.S. Pat. No. 5,130,230 discloses that the blood substitute comprises "an aqueous solution of electrolytes at physiological concentration, a macromolecular oncotic agent, a biological buffer having a buffering capacity in the range of physiological pH, simple nutritive sugar or sugars, magnesium ion in a concentration sufficient to substitute for the flux of calcium across cell membranes. The blood substitute also includes the forgoing solution and a cardioplegia agent such as potassium ion in a concentration sufficient to prevent or arrest cardiac fibrillation." Thus potassium ion at physiological concentration is part of the base solution of the disclosed blood substitute. The specification also discloses that concentration of cations including Mg++, Ca++ and K+ in excess of that normally found in mammalian blood are suitable for exerting a cardioplegia effect. Lastly the specification discloses that the blood substitute may be used as a blood volume expander and that "(f)urthermore if the blood substitute according to the invention is used as a blood volume expander in a subject at non-hypothermic temperatures, the cardioplegia agent described . . . will generally be omitted so that normal cardiac function can be maintained." From the forgoing it is clear that the blood substitute when used as a blood volume expander at normal body temperatures contains K+ at physiological concentrations but not in concentrations sufficient to cause cardioplegia.

Commercial products used for the treatment of hypovolemic patients are known and include Hespan® (6% hetastarch 0.9% Sodium chloride Injection [Dupont Pharmaceuticals, Wilmington Del.]), Pentaspan (10% pentastarch in 0.9% Sodium chloride Injection [Dupont Pharmaceuticals, Wilmington Del.]) and Macrodex (6%

Dextran 70 in 5% Dextrose Injection or 6% Dextran 70 in 0.9% Sodium chloride Injection [Pharmacia, Inc. Piscataway, N.J.]) and Rheomacrodex (10% Dextran 40 in 5% Dextrose Injection or 10% Dextran 40 in 0.9% Sodium chloride Injection [Pharmacia, Inc. Piscataway, N.J.]). These products are known to the medical community for particular FDA approved indications and are extensively described in the volume entitled Physicians' Desk Reference, published annually by Medical Economics Company Inc..

Water-soluble and aqueous colloid preparations of vitamin K are known and are sold respectively under generic names menadiol sodium diphosphate (tradename SYNKAVITE®) and phytonadione MSD, USP (tradename AquaMEPHYTON®) by Roche Labs and Merck Sharp & Dohme, respectively.

SUMMARY AND OBJECTS OF THE INVENTION

It is an object of the invention to provide a blood plasma expander comprising a water soluble polysaccharide oncotic agent supplemented with calcium chloride at physiological concentration.

It is a further object of the invention to provide a blood plasma expander comprising a water soluble polysaccharide oncotic agent supplemented with sodium chloride at physiological concentration and magnesium ion at sub-physiological concentration.

It is a yet further object of the invention to provide a blood plasma expander comprising a water soluble polysaccharide oncotic agent supplemented with sodium chloride at physiological concentration and magnesium ion at sub-physiological concentration and potassium ion at sub-physiological concentration.

Another object of the invention to provide a blood plasma expander comprising at least two water soluble polysaccharide oncotic agents one of which is eliminated from the circulation slowly and the other of which is eliminated from the circulation quickly.

Yet another object of the invention is to provide a buffered blood plasma substitute comprising a water soluble polysaccharide oncotic agent.

A yet further object of the invention is to provide a blood plasma substitute comprising a water soluble polysaccharide oncotic agent buffered by lactate and supplemented with sodium chloride at physiological concentration.

Still another object of the invention is to provide a blood plasma substitute comprising a water soluble polysaccharide oncotic agent buffered by lactate and sodium bicarbonate and supplemented with sodium chloride at physiological concentration.

Still yet another object of the invention to provide a blood plasma substitute comprising at least two water soluble polysaccharide oncotic agents one of which is eliminated from the circulation slowly and the other of which is eliminated from the circulation quickly, wherein the blood plasma substitute is buffered and supplemented with sodium chloride at physiological concentration.

It is yet another object of the invention to provide a method for expanding the blood volume of a subject in need thereof by administering intravenously to such subject a blood plasma expander comprising a water soluble polysaccharide oncotic agent supplemented with sodium chloride and calcium chloride at physiological concentration.

Still a further object of the invention is to provide a method for expanding the blood volume of a subject in need thereof by administering intravenously to such subject a blood plasma expander comprising at least two water soluble polysaccharide oncotic agents one of which is eliminated from the circulation slowly and the other of which is eliminated from the circulation quickly.

Yet another object of the invention is to provide a method of substituting the blood plasma of a subject in need thereof by administering intravenously to such subject a blood plasma substitute comprising a water soluble polysaccharide oncotic agent buffered by lactate and supplemented with sodium chloride at physiological concentration.

Still yet another object of the invention is to provide a method of substituting the blood plasma of a subject in need thereof by administering intravenously to such subject a blood plasma substitute comprising a water soluble polysaccharide oncotic agent buffered by lactate and sodium bicarbonate and supplemented with sodium chloride at physiological concentration.

Yet still another object of the invention is to provide a method of substituting the blood plasma of a subject in need thereof by administering intravenously to such subject a blood plasma substitute comprising at least two water soluble polysaccharide oncotic agents one of which is eliminated from the circulation slowly and the other of which is eliminated from the circulation quickly buffered by lactate and optionally with sodium bicarbonate and supplemented with sodium chloride at physiological concentration.

DESCRIPTION OF THE INVENTION

The present invention comprises a mixture of components including at least one water soluble polysaccharide oncotic agent and preferably a mixture of two or more water soluble polysaccharide oncotic agents wherein one is capable of relatively quick elimination from the circulation and the other is capable of relatively slow elimination from the circulation. The mixture also generally includes sufficient sodium chloride to yield a physiologic concentration approximating that of human serum and sufficient calcium ion to yield a concentration in a range of 80 to 110 milligrams per liter.

In addition as an aqueous solution the forgoing mixture may also include magnesium ion in a concentration range which is less than 1 mEq and at least 0.5 mEq/l. Furthermore, optionally the forgoing mixture may include potassium ion at a concentration range of about 2 to 3 mEq/l. Both of the forgoing concentration ranges of magnesium ion and potassium ion are considered to be sub-physiologic for primates and especially human beings.

In greater detail, the present invention comprises a mixture of components which when placed in aqueous solution may be used to expand the plasma volume of a subject in need thereof. The forgoing components may be provided as a dry sterile mixture to which sterile diluent such as water, saline solution or dextrose solution may be added to form an aqueous solution. If provided as a dry sterile mixture, the materials may be provided in a sterile container suitable for mixture with sterile diluent such as sterile water, sterile saline or sterile dextrose solution. Alternatively the mixture of materials may be provided in a sterile container as an aqueous solution.

If the mixture of components according to the invention is provided as a dry sterile mixture suitable for fluid addition by a sterile saline solution, the amount of chloride salt of sodium in the dry mix is adjusted or omitted in amount equal to the sodium chloride contained in the sterile saline solution used. If the mixture according to the invention is provided as an aqueous solution, it is preferable to provide the solution as a sterile solution in a sterile container. Alternatively, the aqueous solution according to the invention may be provided as a non-sterile solution and may be subsequently sterile filtered into or autoclaved in sterile containers.

In another embodiment of the invention, the solution may be provided as a small volume sterile aqueous solution containing the mixture of components according to the invention in high concentration, which when mixed with a predetermined volume of an existing commercially available sterile oncotic solutions such as a commercial preparation of high molecular weight hydroxyethyl starch sold under the trade name Hespan® (DuPont) or low molecular weight hydroxyethyl starch sold under the trade name Pentaspan (DuPont) provides a solution with the buffer or buffers and ions in the concentrations described herein in accordance with the invention.

For purposes of the further description of the invention, the mixture of components according to the invention will be discussed as an aqueous solution. From the following description of the invention it is expected that one ordinarily skilled in the art would be enabled to provide the mixture as a dry mixture and make the adjustments to amounts of sodium chloride and or dextrose as necessary to accommodate the amounts of sodium chloride found in normal saline solution for injection of a dextrose solution for injection, which may be used as a diluent for the dry mixture according to the invention.

The polysaccharide oncotic agents of the forgoing mixture of components are ones that are water soluble. By water soluble is meant that the polysaccharide will dissolve in water readily or with stirring or shaking. By water soluble oncotic agent is meant water soluble molecules which when dissolved in the fluid phase of circulating plasma in a living subject are of a size sufficient to prevent their immediate loss from the circulation by traversing the fenestration of the capillary bed into the interstitial spaces of the tissues of the body. The term polysaccharide oncotic agent thus does not include such polysaccharides as chitin since chitin is not soluble in water.

Polysaccharides that are water soluble and can act as oncotic agents are generally characterized as glucan polymers. In general, it is preferred that the water soluble polysaccharide oncotic agent is a glucan polymer that is non-antigenic.

Hetastarch, which is a tradename for hydroxyethyl starch, is a glucan polymer which can act as an artificial colloid when dissolved in water. Hydroxyethyl starch is derived from a waxy starch composed almost entirely of amylopectin with hydroxyethyl ether groups introduced into glucose units of the starch and the resultant material is hydrolysed to yield a product with a suitable molecular weight. The molar substitution of the hydroxyethyl moiety is 0.7 which means hydroxyethyl starch has 7 hydroxyethyl groups for every 10 glucose units. The average molecular weight of hydroxyethyl starch is 480,000 with a range of 400,000 to 550,000 and with 80% of the polymers falling in the range of 30,000 to 2,400,000. Hydroxyethyl groups are attached by ether linkage primarily at C2 of the glucose unit and to a lesser extent the C3 and C6 position. The glucose units are joined primarily in alpha (1---4) linkage with occasional 1--6 branches. The colloid properties of a 6% solution (wt/wt) of Hydroxyethyl starch approximates that of human serum albumin, with approximately 33% of a 500 ml intravenous dose eliminated in the urine after 24 hours. Approximately 10% of the dose remains circulating after 1 week. As used herein Hydroxyethyl starch is referred to as high molecular weight hydroxyethyl starch.

Pentastarch is another glucan polymer which can act as an artificial colloid when dissolved in water. Pentastarch is also derived from a waxy starch composed almost entirely of amylopectin with hydroxyethyl ether groups introduced into glucose units of the starch and the resultant material is hydrolysed to yield a product with a suitable molecular weight. The molar substitution of the hydroxyethyl moiety is 0.45 which means pentastarch has 45 hydroxyethyl groups for every 100 glucose units. The average molecular weight of pentastarch is approximately 264,000 with a range of 150,000 to 350,000 and with 80% of the polymers falling in the range of 10,000 to 2,000,000. Hydroxyethyl groups are attached by ether linkage primarily at C2 of the glucose unit and to a lesser extent the C3 and C6 position. The glucose units are joined primarily in alpha (1---4) linkage with occasional 1--6 branches. As used herein pentastarch is referred to as low molecular weight hydroxyethyl starch.

Other polysaccharide derivatives may be suitable as oncotic agents in the solutions according to the invention including hydroxymethyl alpha substituted (1---4) or (1---6) polymers. Cyclodextrins such as hydroxypropyl substituted $\beta$ or $\gamma$ cyclodextrin may be suitable as oncotic agents in the blood substitute according to the invention.

D-glucose polymers that are soluble in water may also be used as the water polysaccharide oncotic agent in the mixture according to the invention. Examples of such D-glucose polymers are Dextran, which is D-glucose linked predominantly in alpha (1----6) linkage. Dextran in a molecular weight range of 30,000 to 50,000 daltons (D) are preferred. Most preferred is Dextran 40 having an average molecular weight of about 40,000 D.

The concentration of the polysaccharide oncotic agent in the solution according to the invention will be sufficient so that a significant amount of the oncotic agent is still circulating in a subject 2 to 5, days after administration of the solution. Accordingly, the solution according to the invention will have a mixture of high molecular weight and low molecular weight polysaccharide oncotic agents the relative amounts of which have been optimized to achieve this effect in this time period. The solution according to the invention will preferably contain a lower or equal concentration of higher molecular weight polysaccharide oncotic agents as compared to the concentration of lower molecular weight polysaccharide oncotic agents. Higher molecular weight polysaccharide oncotic agents such as high molecular weight hydroxyethyl starch and dextran 70 are generally eliminated from the circulation at a slower rate than lower molecular weight polysaccharide oncotic agents such as low molecular weight hydroxyethyl starch and dextran 40. High molecular weight hydroxyethyl starch is eliminated from the circulation of a human being slowly. Approximately 33% of a 500 ml infusion of 6% high molecular weight hydroxyethyl starch is eliminated from the circulation after 24 hours, with approximately 10% of the dose remaining in the circulation after 2 weeks. Low molecular weight hydroxyethyl starch is eliminated from the circulation of a human being quickly. Approximately 70% of a 500 ml infusion of 10% low molecular weight hydroxyethyl starch is eliminated from the circulation after 24 hours, with approximately 20% of the dose remaining in the circulation after 1 week. Elimination time for 6% dextran 40 and similar low molecular weight water soluble polysaccharide oncotic agents are similar.

When Dextran 40 or low molecular weight hydroxyethyl starch is used in the solution according to the invention its concentration is in a range of 6.0 to 8.5%. A solution comprising about 8% Dextran 40 (wt/v) or about 80 grams (g) per liter (1) of water is generally used. When Dextran 70 or high molecular weight hydroxyethyl starch is used in the solution according to the invention its concentration is in a range of 5.5% to 6.5%. A solution comprising about 6% high molecular weight hydroxyethyl starch (wt/v) or about 60 grams (g) per liter (1) of water is generally used.

When it is necessary to treat a subject who has lost a significant amount of blood, generally up to about 30% to 40% of blood volume with a plasma expander, the forgoing mixture may be administered intravenously or intravascularly as a sterile aqueous solution. In another embodiment of the invention, the oncotic agent is a mixture of high molecular weight water soluble polysaccharide, such as high molecular weight hydroxyethyl starch or dextran 70, and low molecular weight water soluble polysaccharide, such as low molecular weight hydroxyethyl starch or dextran 40. In this embodiment of the invention which may be particularly useful when it is not possible to transfuse a subject with whole blood quickly, the amount of high and low molecular weight hydroxyethyl starch is adjusted to initially stabilize the colloid osmotic pressure of the subject's blood and then to gradually remove the water soluble oncotic agent as the patient begins to replenish circulating serum proteins.

Solutions according to the invention having this composition will typically include high molecular weight hydroxyethyl starch in a range of from 5 to 40 grams per liter and dextran 40 or low molecular weight hydroxyethyl starch in a concentration of 20 to 75 grams per liter; however the concentration of the two water soluble oncotic agents together will generally not exceed 80 grams per liter. It is believed that a solution comprising about 20 grams per liter high molecular weight hydroxyethyl starch and about 50 grams per liter of dextran 40 or about 50 grams per liter of low molecular weigh hydroxyethyl starch is desirable. A solution comprised of about 30 grams per liter high molecular weight hydroxyethyl starch and about 30 grams per liter of dextran 40 or about 30 grams per liter of low molecular weight hydroxyethyl starch may be preferred.

In determining the amount of the two oncotic agents in the solution according to the invention, the amounts of the two agents are adjusted to maintain oncotic balance without infusing so much of the oncotic agent that the plasma becomes hyperoncotic and circulating serum proteins are removed from the circulation by hepatic absorption or renal excretion or other physiological mechanisms. Thus it is important that the high molecular weight hydroxyethyl starch or dextran 70 and low molecular weight hydroxyethyl starch or dextran 40 should not together exceed about 8% weight/volume percent. Solutions exceeding this concentration of oncotic agent may be physiologically hyperoncotic leading either to removal of serum protein from the circulation or an inhibition of their production. Since high molecular weight hydroxyethyl starch and dextran 70 are not quickly eliminated from the circulation the amount of these oncotic agents will generally not be more than 75% of the total weight of the water soluble oncotic agents in the solution. By using a high molecular weight oncotic agent in the solution in combination with a low molecular weight solution, the addition of the solution to a subject's circulation either as a plasma expander after trauma or surgery, or as a blood substitute when more than 30% of the subject's circulating volume is made up of the blood substitute, the subject's circulating oncotic pressure is quickly stabilized, fluid exchange between the circulating blood compartment and the interstitial spaces is minimized, and edema is curtailed. Furthermore, the rate of elimination of the low molecular weight oncotic agent is sufficiently quick that oncotic balance can be maintained without inhibiting the subject's production of new serum proteins, while at the same time the rate of elimination of the high molecular weight oncotic agent is sufficiently slow that the polysaccharide oncotic agent is able to maintain oncotic balance until sufficient protein has been produced after substantially complete elimination of the low molecular weight polysaccharide oncotic agent.

The solutions according to the invention with calcium and magnesium ions provided by the solution have the advantage of providing essential ions required for the patient's blood to maintain its ability to clot. This advantage may be significant to a patient suffering from a hemorrhage or internal bleeding with concomitant loss of blood pressure due to decreased blood volume. In these patients the administration of conventional plasma expanders such as Hespan®, Pentaspan®, Macrodex® and Rheomacrodex® may lead to dilution of blood plasma proteins and ions essential to the formation of blood clots which may be life saving particularly for trauma patients. If the conventional plasma expanders are used, dilution of the blood proteins and electrolytes essential for clotting may have fatal consequences. By administering the solution according to the invention, the provision of essential electrolytes will lead to a greater preservation of the ability of the patient's blood to clot if necessary.

In the solution according to the invention the magnesium ion concentration will range between 0.5 and 0.9 mEq/l. Magnesium ion is generally sequestered intracellularly in an intact mammalian subject; however in the event of trauma which damages tissues, magnesium ion concentration will increase. Thus it is desirable to administer the solution according to the invention with magnesium ion concentrations on the low end of this range when tissue damage has occurred. Typically this will be in situations wherein the solution is administered to maintain the blood volume of a trauma victim. By contrast, when the solution is used to substitute for the blood of a subject, such as when surgical procedures at low temperature are carried out, it is desirable to administer the solution according to the invention with magnesium ion concentrations at the high end of the range. In either case the concentration of the electrolyte magnesium ion is one that is generally considered to be less than physiological. When a subject's blood magnesium ion concentration falls below normal several problems may occur including tetany and irregular heartbeat. In maintaining electrolyte levels in normal human subjects, magnesium ion concentration of less than 0.5 mEq/l are considered to be "panic levels" ie.—concentrations which require immediate intervention and administration of available high concentration magnesium ion containing solutions to normalize the magnesium ion concentration. The normal physiological range for magnesium ion in blood is generally considered to be 1–2 mEq/l. Thus the solutions according to the invention unexpectedly use magnesium ion concentrations that are less than physiological to maintain subject blood volume or blood substitution at low temperature. This is unlike the teaching of prior teachings such as U.S. Pat. Nos. 4,923,442 and 5,130,230 and standard nursing texts on maintenance of proper electrolyte balance.

It has been discovered that the utility of the forgoing solutions which may be used as plasma volume expanders, may be extended by also including a sufficient amount of a water soluble preparation or aqueous colloid suspension of vitamin K to stimulate the liver to produce blood serum proteins essential to maintaining normal blood clotting function, usually expressed as the time it takes for a standard volume of whole blood or blood plasma to clot. In general, a concentration of vitamin K in the solution sufficient to deliver about 5 to 10 mg of vitamin K to the subject is required in the solution according to the invention. Thus if 2–3 liters of solution are delivered to the patient's circulation a concentration of 2 to 3 mg of vitamin K per liter will be used. It is believed that a concentration of about 2.5 mg/l vitamin K is optimal for this purpose.

The forgoing solutions may also be augmented, optionally, by a small amount of potassium ion generally in a concentration range between 2 to 3 mEq/l. The use of potassium ion in this concentration range may be indicated in individuals who have lost a substantial amount of blood but who have not been subject to extensive tissue trauma or whole blood transfusion. In both of these latter conditions, significant amounts of potassium ion may be released into the blood stream by lysis of blood cells or tissue cells. If high concentrations of potassium ion released by such trauma or transfusion prevail in the blood for a significant period of time, particularly as a result of lowered renal perfusion and filtration rates because of low blood volume, it may be desirable to omit potassium ion from the solution administered to such patients. On the other hand if normal potassium concentrations are present in the subject's remaining circulating blood, it will be desirable to include potassium in the solution according to the invention.

One of the problems in treatment of hypovolemic patients who have lost substantial amounts of blood, generally greater than 30% of their normal blood volume, is the need to provide in addition to essential electrolytes, and reasonable oncotic balance, sufficient ability to maintain pH and nutrition of the central nervous system, while at the same time permitting the remaining blood in the subject to function normally. Patients who have lost 30% or greater of their blood volume and who are treated with Hespan® frequently experience breaking of their red blood cells or hemolysis in addition to other problems associated with extreme hemodilution such as reduced clotting time and prothrombin levels.

In individuals who have lost more than 30% of their blood it is desirable to further augment the forgoing solutions as described further herein below with respect to buffering capacity to maintain proper pH, assimilable sugar and, particularly when it is difficult to find a matching blood donor or whole blood transfusion would be otherwise difficult, a material which stimulates the formation of blood proteins necessary for proper blood clotting. In particular Vitamin K in a form which may be administered in aqueous solution is included at a concentration effective to stimulate hepatic synthesis of blood coagulation factors including prothrombin (factor II) proconvertin (factor VII), thromboplastin (factor I) and Stuart factor (factor X).

To provide buffering capacity the forgoing solution will include a sufficient amount of buffer to permit effective buffering of the circulating blood in a pH range around 7.4. In some uses, the buffer is sodium lactate at a concentration in a range of 10 to 30 mM, preferably about 28 mM. Sodium lactate is preferred because lactate is a compound naturally occurring in the body. Additionally, other suitable buffers usable in lieu of lactate are small organic acid ions that may be metabolized such as acetate, pyruvate, gluconate and succinate. Citrate should not be used since it adversely affects the ability of whole blood to clot. NaHCO$_3$ (sodium bicarbonate) will be provided as a buffer in addition to sodium lactate, in a concentration of about 5 to 10 milliMolar (mM). It is also possible to use a biological buffer such as HEPES or a balanced solution of Trizma base and Trizma HCl in lieu of lactate or bicarbonate. When Trizma base/Trizma HCl is used to provide buffering, these components are added in the amount of about 0.83 and 2.86 grams per liter of solution respectively; however biological buffers are preferably not used unless the oncotic agent is provided by a mixture of water soluble high and low molecular weight polysaccharides.

Vitamin K which is compatible with aqueous media for injection will be preferred in the solution according to the invention. Preparations of this general type are known and are sold as pharmaceutical preparations in their own right under various names such as menadiol sodium diphosphate, which is a synthetic water-soluble derivative of menadione vitamin $K_3$ (Roche, Nutley N.J.) and phytonadione which is a clear aqueous dispersion of vitamin $K_1$ (Merck Sharp & Dohme). In general the concentration of aqueous vitamin K in the solution according to the invention will be sufficient to deliver between 5 to 10 milligrams to the subject. The wide range of vitamin K concentration is necessary to accommodate patients in age and weight from infant to adult.

The solution according to the invention for administration to patients who have lost more than 30% of their blood volume will also include an easily assimilable sugar. In general dextrose (glucose) is preferred in a concentration sufficient to sustain a substantially constant glucose serum concentration in the subject. In general a concentration range from about 5 to 10 mM glucose will be used.

When used as a blood plasma expander in a hypovolemic subject, the solution according to the invention will be administered in an amount up to about 30% of the average blood volume of an average subject. If the subject is the size of an average adult male human being the average blood volume is about 5000 ml and the volume of the solution according to the invention will be up to about 1500 ml. The composition of the solution according to the invention used as a blood plasma expander will generally comprise an aqueous solution of water soluble polysaccharide oncotic agent, with dissolved Sodium chloride at physiologic concentration (about 0.9% or 154 mM), calcium chloride at a concentration of about 2.5 mM and optionally magnesium chloride in a concentration range which is less than 1 mEq/l and at least 0.5 mEq/l. In general a magnesium chloride concentration of about 0.475 mM is preferred. The water soluble polysaccharide may be high molecular weight hydroxyethyl starch dextran 70 or dextran 40 in a concentration of about 60 grams/liter. Optionally, the forgoing mixture may include potassium ion at a concentration range of about 2 to 3 mEq/l. In an additional option the solution may also include aqueous vitamin K in a concentration sufficient to deliver between 5 to 10 milligrams to the subject. When administered to a subject the solution according to the invention will be administered intravenously or intravascularly as a sterile solution by a continuous fast infusion.

When used as a blood replacement in a severely hypovolemic subject or when used in a procedure in which the subject blood is deliberately removed, the solution will be administered as a sterile solution in an amount exceeding 30% of the average blood volume and will generally exceed 1500 ml. The composition of the solution according to the invention used as a blood replacement will generally comprise the components in the amounts described in the preceding paragraph. If administered to a mammalian subject that has been chilled to hypothermic body temperatures, (generally 5 or more degrees Centigrade below normal body temperature) potassium ion may be completely omitted from the solution or may be present in sub-physiological amounts up to about 3 mEq/l according to the invention. If the solution is administered to a subject that is at normal body temperature, the solution according to the invention may include potassium ion at a concentration range of about 2 to 3 mEq/l.

In addition, whether administered as a blood replacement to a hypothermic subject or a subject at normal temperature, the solution will also contain a buffer. A preferred buffer is lactate at a concentration of about 28 mM. Sodium lactate is preferred because lactate is a compound naturally occurring in the body. Alternatively, the buffer will also include a sufficient amount of $NaHCO_3$ to permit effective buffering of the circulating blood in a pH range around 7.4. In general, $NaHCO_3$ will be provided in a concentration of about 5 to 10 milliMolar (mM), and preferably at about 5 mM particularly if the subject's body temperature is 5 degrees Centigrade below normal or lower when the solution is administered as a blood plasma substitute or blood plasma expander.

Prior art blood substitute solutions generally teach that it is desirable to provide a buffer that is a biological buffer in a solution having, prior to administration to a subject, a pH range of about 7.2 to 7.8. Such buffers are exemplified by HEPES, MOPS, TRIS, and other similar buffering salts. Such biological buffers are very expensive, in contrast to the cost of the components in the solutions according to the invention. The buffering capacity of these biological buffers is greatest in the pH range 7.2 to 7.8 which is the pH range in which mammalian subjects normally regulate blood pH. One great disadvantage of these biological buffers is that, although they buffer best at normal physiological pH in vitro, most are as yet not generally regarded as safe for human administration and none has been used clinically as an integrated component in a large volume parenteral solution. By contrast, it has been found by the inventors that, suprisingly, small organic acids provided as salts such as sodium lactate and sodium bicarbonate can be used in the plasma extender and blood plasma substitute solutions according to the invention to stabilize the pH of the subject treated with them, even though lactate and bicarbonate do not chemically buffer the pH of these solutions if the pH is measured in vitro prior to administration. (A 5 mM solution containing a biological buffer, such as HEPES, has far greater buffering capacity.) Suprisingly, even though the pH of the solutions prior to administration to a subject may not be in the physiological range of 7.2 to 7.8 the pH of the solution circulating in the subject remains physiological. In the case of lactate alone, the average pH is about 5.5 prior to administration. In the case of bicarbonate as buffer, the solutions according to the invention have a pH greater than pH 8 at room temperature prior to administration. As used herein such small organic acids, exemplified by lactate and bicarbonate, and also acetate and pyruvate are physiological buffers because they are able to maintain a subjects circulating fluids at pH in the physiological range.

The use of these small organic acid salts to stabilize the pH in the solutions according to the invention when circulating in a subject is particularly advantageous when the solution is used to substitute a significant amount of a subject's missing blood volume. Thus the use of small organic acid salts as buffers in the solutions of the invention is particularly advantageous when the solution is used to replace or substitute for blood volumes in excess of 30% of the subjects normal circulating blood volume. By using small organic acid salts as buffers, such as sodium lactate or sodium bicarbonate, it is possible to perfuse a subject for many hours using the solutions according to the invention without encountering the hazard of uptake and sequestration of chemical compounds such as HEPES, MOPS, TRIS and other similar buffering salts used in prior art solutions such as those disclosed in Segall et al., U.S. Pat. Nos. 4,923,442 and 5,130,230. Unexpectedly, it has been found that despite an initial pre-administration pH of about 5.5, the solutions according to the invention in both primate and rodent models are able to maintain pH of the blood after infusion of 7.2 to 7.8 even when used to substantially and completely replace most or all of the circulating blood of a subject.

In a further embodiment of the invention, Applicants have discovered that the small molecule organic acid salt is preferably sodium lactate in a concentration sufficient to maintain the solution at a pH of about 5.5 prior to administration, provided that the volume of blood to be replaced is no greater than about 30% of the blood volume and is administered at normal mammalian body temperatures. It is also preferred to supplement the lactate as buffer in the solution with sodium bicarbonate when the solution is used to substitute more than 30 percent of the subject's blood volume, particularly if this substitution is carried out under conditions wherein the subject is maintained at temperatures between 7 degrees centigrade below normal temperature and about 1 degree centigrade.

This discovery is particularly important when one is using the solution to maintain a subject during procedures in which the subject is cooled to core body temperatures at which the subject is not itself capable of maintaining normal physiological homeostatic mechanisms such as those which maintain blood pH between 7.5 and 7.8. Lactate infused initially in the solution according to the invention, does not sufficiently buffer at low temperature. Therefore, in using the solution according to the invention to substitute the blood of a subject under cold hypothermic conditions, it is advantageous to use the solution containing sodium lactate to initially substitute for the subject's blood, and as the subject's blood is replaced to begin substitution using sodium bicarbonate in addition to sodium lactate since the addition of sodium bicarbonate yields a more stable pH in a physiological range. Thus, complete substitution may be accomplished using a system of two solutions, the initial solution comprising sodium lactate as buffer and the subsequent solution using sodium bicarbonate and sodium lactate.

When used as a plasma extender, which in general is in situations where 30% or less of the subject's normal blood volume is being added (usually after blood loss due to trauma or surgery), the solution according to the invention will usually be administered to a subject at normal body temperature for that mammalian subject. It is preferred that the solution according to the invention, when used as a plasma extender and administered at about normal body temperature, have only lactate as a buffer, which is provided in the solution as sodium lactate. At normal body temperatures, lactate may be eventually metabolized by the subject leaving assimilable (or easily excreted) sodium ion.

When used as a plasma substitute, which in general is in situations where more than 30% of the subject's normal blood volume is being perfused into the subject, usually when the subject's blood is being removed at the same time as the solution according to the invention is administered, the solution according to the invention will usually be administered to a subject that has been chilled to a body temperature below normal, usually 7° C. or more below the normal temperature for that mammalian subject. It is preferred that the solution according to the invention, when used as a plasma substitute and administered at such subnormal body temperatures, have in addition to lactate as a buffer, sodium bicarbonate ($NaHCO_3$). In practice, if the process of replacing the subject's blood is started before the subject's body temperature is substantially below normal, the solution according to the invention with only sodium lactate as buffer will be administered. As body temperature falls below normal the solution according to the invention with sodium lactate and sodium bicarbonate will be administered to the subject. Furthermore, during the period of time that the subject is maintained at below normal temperature, it will be periodically perfused with fresh solution according to the invention containing both sodium lactate and sodium bicarbonate as buffer. The solution according to the invention containing both sodium lactate buffer and sodium bicarbonate solution is preferred when the subject is to be used for the purpose of harvesting body organs for eventual transplant and organ preservation is of paramount importance. In addition this same solution may be used to perform surgery on a subject when it is necessary to reduce the subject's temperature to slow metabolic activity and the removal of blood is required to optimize the condition of the surgical field.

In one embodiment of the invention 0.9% saline, Ringer's lactate, Plasmalyte, Normasol or other commonly used crystalloid solution can be used to replace up to 50% to 100% of the subject's blood instead of the lactate-buffered solution. This solution must then be rapidly replaced by the lactate and bicarbonate buffered form of the invention.

The solutions according to the invention containing lactate have an initial pH prior to administration to a subject of about 4 to 6.0. It is possible to more easily terminally heat sterilize the solutions according to the invention at pH 5.5, without adversely affecting the status of the polysaccharide oncotic agents or other carbohydrates in the solution which tend to caramelize when terminally sterilized at pH exceeding 7.0. Sodium bicarbonate may limit the ability of the solution to be terminally heat sterilized. To facilitate use of the solutions according to the invention the solution may be supplied as a kit including a terminally heat sterilized solution including all the components of the solution according to the invention in a ready to use container except sodium bicarbonate and a second sterile container of premeasured sterile sodium bicarbonate solution which may be added using sterile technique to the ready to use solution.

Less preferred buffer in the solutions according to the invention is a biological buffer such as HEPES or a balanced solution of Trizma base and Trizma HCl in lieu of bicarbonate and/or lactate. When Trizma base/Trizma HCl is used to provide buffering, these components are added in the amount of about 0.83 and 2.86 grams per liter of solution respectively and are preferably used only when the water soluble polysaccharide oncotic agent is a combination of high molecular weight and low molecular weight polysaccharides.

Also included in the solution according to the invention when administered as a blood replacement, the solution will include an assimilable sugar, preferably dextrose at a concentration of about 5 mM. When administered as a blood replacement, the solution may be quickly infused through a venous cannula or other indwelling device able to permit large volume infusion. The blood pressure of the subject may be monitored so that central venous pressure remains below 10 millimeters of mercury. If pressure begins to increase, a volume of blood may be removed through the venous cannula and the pressure equilibrated at an acceptable level. If desired the solution according to the invention may be perfused into the subject by means of a pump and closed circuit including a reservoir of the solution according to the invention until the subject's blood is partially or fully replaced with the solution according to the invention as desired.

At normal mammalian temperature, a trauma or surgical patient's blood volume is first stabilized and then brought up to normal volume using at least one of a number of solutions in which a water soluble polysaccharide oncotic agent in solution with essential cations $K^+$ and $Mg^{++}$ at subphysiologic concentrations and a simple salt of an organic acid as a physiologically active buffer, such as sodium lactate, and a nutritive sugar such as glucose are provided. The essential cations and other electrolytes are provided by the following (in mM concentrations): NaCl 110–120, $MgCl_2$ no greater than 0.45, $CaCl_2$ 2.5 KCl 3 or less. Glucose is provided at a concentration range of about 5–10 mM and sodium lactate is provided at a concentration of about 28 mM. The water soluble polysaccharide oncotic agent may be provided in a total concentration of about 6% wt/volume (g/l).

As described above the polysaccharide oncotic agent may consist of a single high molecular weight or low molecular weight agent. High molecular weight oncotic agents are high molecular weight hydroxyethyl starch (HmHES) and dextran 70. Low molecular weight oncotic agents are low molecular weight hydroxyethyl starch (LmHES) and dextran 40. When the water soluble polysaccharide oncotic agent is a mixture of high and low molecular weigh oncotic agents, each will be provided at essentially equal concentration. Thus the water soluble polysaccharide oncotic agent may in the solution according to the invention consist of 6% HmHES, 6% LmHES, 6% dextran 70 or 6% dextran 40. Alternatively the water soluble oncotic agent may in the solution according to the invention consist of about 3% of two of each of the forgoing polysaccharide oncotic agents. As explained above, the solutions having mixed polysaccharide oncotic agents in which one is high molecular weight and one is low molecular weight are advantageous because each of the oncotic agents is eliminated from the circulation at different rates. Thus, after infusion into a subject the combined oncotic agents immediately stabilize the volume and colloid osmotic pressure of the subjects' circulating blood compartment. As the subject eliminates one of the two oncotic agents more quickly than the other, while at the same time producing replacement serum proteins, the colloid osmotic pressure of the subject is better maintained.

In another embodiment of the invention, the oncotic agent of the solution is provided in whole or in part by a serum albumin appropriate to the species in to which the solution according to the invention is to be infused or perfused. If human serum albumin (HSA) is to be used, HSA which has been rendered suitable for parenteral administration by heat treatment or some other procedure is preferred. Using HSA for purposes of the following discussion should not be understood to limit the invention to the use of HSA, since HSA would be appropriate for human and possibly some other primate subjects based on similarity or identity of the amino acid sequences of HSA. In species in which HSA would be immunogenic, an other immunologically compatible serum albumin would be used.

In the solution according to the invention, the HSA is provided alone at concentrations of up to 6% or in combination with one or more of the water soluble polysaccharide oncotic agents. If it is provided with the polysaccharide oncotic agents, the concentration of albumin will generally be no greater than 4% (40 g/l). It is preferred that the mixture of HSA and polysaccharide oncotic agent consists of albumin and a High molecular weight polysaccharide oncotic agent such as dextran 70 or HmHES. The ratio of polysaccharide oncotic agent to HSA in these two-oncotic agent solutions will range between 1 to 1 and 1 to 2, or, on a concentration basis between about 3% (w/v) polysaccharide oncotic agent to 3% (w/v) HSA and 2% (w/v) polysaccharide oncotic agent to 4% (w/v) HSA.

It is particularly advantageous to use albumin in the solutions according to the invention. As a mammalian blood protein, albumin has several important physiological functions which are more completely preserved when the solutions according to the invention comprise albumin. As a blood protein, albumin is amphoteric at physiologic pH and contributes to the maintenance of buffering capacity of the blood. In addition, albumin is an important ion-binding protein which binds to essential divalent cations, particularly calcium ion. Thus by using albumin as an oncotic agent in the solutions according to the invention, particularly the two oncotic agent solutions, the capacity of the subject to maintain normal circulating and tissue calcium ion concentrations is enhanced over solutions such as HetaStarch, Pentastarch, Rheomax and other similar commercial preparations. Approximately 50% of the Calcium ion in the mammalian circulation is bound to protein and albumin comprise approximately 60% of the circulating blood proteins.

In addition, albumin binds to thyroxin, a hormone essential to the regulation of normal metabolic activity in the mammal. Thus by using albumin in the solution according to the invention, the subjects' ability to maintain normal levels of metabolic activity, by providing a repository for circulating thyroxin is believed to be enhanced. A further advantage of albumin in the solution according to the invention is the capacity of the body to eliminate this serum protein metabolically. Thus by including albumin as an oncotic agent in the solution according to the invention, the subject is able to more rapidly adjust the colloid osmotic pressure of the circulating plasma-like substance of the invention by hepatic catabolism in addition to any renal excretory capacity. By including albumin in the solution, the risk of causing the subject to become hyperoncotic as a result of administering the solutions according to the invention is thereby reduced.

In the solution according to the invention in which colloid osmotic pressure of the solution is provided by two water soluble polysaccharide oncotic agents or by a water-soluble oncotic agent and HSA, the solution may be further augmented by sodium ion, magnesium ion, calcium ion, and chloride ion. In each instance the exact concentration of the ion will vary. In general, if the subject into which the solution is infused has experienced significant trauma to tissues, which ordinarily leads to release of intracellularly sequestered ions into the interstitial fluid and ultimately into the serum component of the blood, it will be desirable to supply the above-mentioned ions at concentrations that are below the normal serum values for such ions. In this situation, ion concentration are achieved by adding preferably chloride salts of these ions to achieve the following concentrations in the solution (in mM) NaCl 110–120, $CaCl_2$ about 2.5, KCl 0–3, and $MgCl_2$ up to 0.45. It will be noted that the concentration of the latter two cations in the solution according to the invention is sub-physiological.

In situations, however, where extensive tissue damage is not expected the concentration of potassium and magnesium ions may be increased by providing preferably the chloride salts of the above mentioned ions to achieve essentially physiologically normal concentrations in the solution as follows (mM): $MgCl_2$ 0.5–1.5 and KCl 4–5, while NaCl and $CaCl_2$ are at the concentrations mentioned above. The concentration of glucose may range between 5 to 10 mM and will generally be at the higher end of this range if extensive trauma is present and at the lower end of this range if extensive trauma is not present.

The buffering capacity of the two-oncotic agent solution mentioned above may be provided by a number of different buffers, including biological buffers and small organic acid molecules as described herein-above. Sodium lactate, sodium acetate, and sodium pyruvate at mM concentrations of about 28 are preferred, particularly in cases in which the solution according to the invention is infused into the subject at body temperatures approximating normal body temperature for the particular mammalian subject. Despite the fact that solutions according to the invention have pH's that are distinctly acidic (pH range 5–6) such solutions are, surprisingly, capable of maintaining essentially normal blood pH when infused into a subject.

Of course the two-oncotic agent solutions of the invention, including those comprised of two water soluble polysaccharide oncotic agents or those comprised of albumin and a water soluble polysaccharide oncotic agent, may also be further augmented with vitamin K as has been disclosed and discussed herein above, preferably with a water soluble formulation of vitamin K in a concentration effective to lead to hepatic production of certain proteins required for blood clot formation.

The forgoing solutions may be particularly useful in establishing normal circulating fluid volume in a patient experiencing intraoperative blood loss or bleeding due to traumatic injury.

In a further embodiment of this invention, amylase or other such starch digesting enzyme, is used when the solution according to the invention using HmHES or LmHES or any of the dextrans, as the water soluble polysaccharide oncotic agent is administered to a subject. Preferably the amylase will have the same amino acid sequence of human amylase, such as human pancreatic or liver amylase enzyme. The amylase enzyme may be obtained from a variety of biological sources but in order to minimize the possibility of disease transmission from materials processed from human sources it may be desirable to use amylase produced as a recombinant protein from a genetically engineered cell such as yeast, insect cells, Chinese hamster ovarian cells or other available cell in culture.

Of course it will be necessary to use a glycosidase that is capable of digesting the glycosidic bonds in the polysaccharide oncotic agent used in the solution so that for example hetastarch, dextran 70 or dextran 40, may be removed from the circulation of the subject to which the solution according to the invention has been administered. If these glycosidases are unlike the human amylase or genetically-engineered human amylase enzymes, they may be antigenic in clinical use.

To minimize the likelihood of immunologic reaction to such non-human glycosidases, the enzyme may be immobilized in an extracorporeal circuit. After blood replacement, with the solution according to the invention the starch-digesting enzyme is administered intravenously or intravascularly at a rate which allows maximum recovery of the plasma protein concentration by digesting the hetastarch or dextran at a rate optimal for starch replacement by plasma protein. Alternatively, if the starch digesting enzyme is immobilized in an extracorporeal circuit, the subjects blood may by circulated through the extracorporeal circuit to be brought into contact with the immobilized starch digesting enzyme where the polysaccharide oncotic agent may be digested into its glucose constituents. Alternatively, starch may be removed through the extracorporeal use of beads or other fixed surfaces, composed of or containing materials, such as monoclonal antibodies, that bind to starch. Lastly, such non-human glycosidases may be conjugated to polyethylene glycol which renders the protein less immunogenic.

This digestion or removal of starch may mitigate the effect whereby the starch, especially the high molecular weight starch such as the HmHES which has a relatively long half-life in the circulation, suppresses the synthesis of plasma protein and deprives the body of blood proteins needed for clotting reactions, transport of nutrients and minerals and other vital functions.

It has also been observed that the crystalloid constituents of the solutions described above, in the absence of starch or albumin oncotic agents have a distinct utility. These constituents include the following salts and glucose as follows (in mM):

NaCL 110–120, KCl 3, $MgCl_2$ 0.45, $CaCl_2$ 2.5, glucose 5–10, and sodium lactate 28. The solution may be optionally augmented with sodium bicarbonate if pH falls below optimum levels. In some embodiments, particularly when extensive trauma to tissues are not present or anticipated the concentrations of the salts and glucose may be in the following ranges (in mM): NaCl 110–120, KCl 4–5, $MgCl_2$ 0.5–1.5, $CaCl_2$ 2.5, and glucose 5. This solution referred to herein below as L solution may be used as a system prime volume when a subject is initially placed on cardiopulmonary bypass, and is especially useful when the subjects circulating blood volume is substantially greater than the system volume of the cardiopulmonary by-pass equipment. Optionally the L solution may be augmented with about 6 to 6.5 g/l of mannitol or other metabolically inactive sugar, and this solution is used as the forgoing L solution.

In situations wherein the system volume of the cardiopulmonary by-pass equipment is substantially greater than the subject's circulating blood volume, the use of L solution has less advantage, since substantial hemodilution generally will lead to a drop in colloid osmotic pressure in the patient. In these circumstances the use of the solutions described above which include the combination of high and low molecular weight water soluble oncotic agents or albumin oncotic agents may be used as a prime solution. These solutions include HL, $D^{70}L$, $D^{40}L$, PL, $H3D^{40}3L$, H3P3L, $D^{70}3D^{40}3L$, $D^{70}3P3L$, AL, H3A3L, or $D^{70}3A3L$. (These solutions are defined herein below in Example 5.) Because, however, the volume of the solution used as a prime, even when the system volume of the cardiopulmonary by-pass equipment is greater than the subject's circulating blood volume does not involve the complete substitution of the subjects blood with the solution of the invention, it may be desirable to adjust the concentration of the oncotic agents to provide only 20 to 40 grams of starch or albumin total per liter of the solution (ie. 2–4% w/v), while maintaining the same ratio of high molecular weight oncotic agents to low molecular weight oncotic agents as described herein above.

If the forgoing solutions, which comprise a water soluble polysaccharide oncotic agent whether at greater or reduced percentages of water-soluble polysaccharide oncotic agents, are administered to a subject, amylase may be subsequently administered to the subject as described above, to digest the starch.

In another embodiment of this invention, at the end of the procedure, human amylase enzyme is mixed with the fluid remaining in the bypass circuit and the starch present from the priming solution is digested with a starch digesting enzyme prior to infusion of the remaining blood cells and plasma. It may be useful at this point to dialyze out the small molecular weight sugars produced by the digestion of the starch by the amylase, or other glucosidase, before introducing this fluid back into the patient as an iv drip. This process will allow the plasma protein levels, as well as the hematocrit, to return rapidly. Since there will be amylase enzyme already in the drip returned to the patient, it may not be necessary to add more enzyme to digest the starch remaining in the patients circulation. In fact, it may be necessary to introduce an amylase inhibitor to slow down the production of sugars by the enzyme.

A further embodiment of the invention utilizes a porous device containing beads, or other surfaces, to which the starch digesting enzyme is bound. The solution remaining in the bypass circuit is circulated through this device, and the enzyme can then digest the starch without any enzyme entering the patient. This reduces the need for an enzyme of human origin. If the entire blood volume is circulated through the device prior to removal of the patient from bypass, then the starch can be digested. The remaining fluid in the circuit can then be placed in an iv bag and returned to the patient in an iv drip. If necessary, some or all of the sugar metabolites of the starch can be removed by dialysis.

Alternatively, the patient can be plasmapherised following removal from bypass, with the immobilized amylase enzyme in the plasmapheresis circuit, and a dialysis unit added to remove excess glucose.

The invention will be better understood in connection with the following examples which are intended by the inventors to be illustrative of the invention but not limiting.

EXAMPLE I

Reviving An Ice-Cold Blood-Substituted Baboon
After Chilling To Near-Freezing

A 7 kg male baboon of the species *Papio anubis* was chilled and blood-substituted to a minimum deep esophageal temperature of 2° C. After reaching that temperature, the animal was warmed, and revived to consciousness.

The baboon was injected im with ketamine. A catheter was inserted in the right cephalic vein, and 2.5% pentothal injected iv The primate was then fitted with an endotracheal tube and placed on flether anesthetic. The animal was shaved, and a Ringer's lactate drip initiated iv, with its rate titrated to the animal's arterial blood pressure. The right femoral artery was catheterized to allow for blood pressure monitoring, and a 3-way stopcock placed in-line to allow arterial blood sampling every 10–60 minutes throughout the entire procedure. A wedge catheter was implanted in the pulmonary artery through the right radial vein.

The extracorporeal circuit was constructed with a hard shell venous reservoir, Biomedicus pump head, hollow fiber membrane oxygenator with integral heat exchanger, flow meter and a secondary in-line heat exchanger added as close to the animal as possible. The circuit incorporates a section between the outflow cannula and the venous reservoir to remove effluent and a 1 L funnel/reservoir to quickly refill the venous reservoir with blood substitute or blood. A cooler to supply the oxygenator's built-in heat exchanger and the secondary heat exchanger with circulating ice water (and warm water) was required. All tubing in contact with blood or blood substitute was sterile. The venous reservoir and circuit was filled with 2 liters of HL solution.

A catheter was placed in the left brachial vein to allow monitoring of central venous pressure (CVP). Arterial blood gases, pH, K+ and hematocrit are measured in each sample, and in some cases, electrolytes, and enzymes as well.

A venous outflow cannula was placed in the left femoral vein. An arterial inflow cannula was placed in the left femoral artery. After the venous cannula was implanted, heparin was injected iv. SoluMedrol (methyl prednisolone) (12 mg/kg) was then injected iv and the eyes coated with a protective ointment. An esophageal tube was inserted, and Maalox administered. The esophageal tube was fitted with a temperature probe for recording deep esophageal temperature. The EKG leads are put in place and the animal was immersed in crushed ice.

Following the onset of cooling, the animal was managed anesthetically light with 2.5% pentothal (at doses between 1–3 cc). When body temperature reaches 30° C., 200 ml of the solution indicated below designated HL was infused in the femoral vein and an equal amount of blood was drained from the arterial cannula and collected sterile for later use. When body temperature dropped below 29° C., anesthetic was discontinued. After chilling to 25° C., the animal was placed on bypass. At that time, the clamps are released which isolate the baboon's circulation from the bypass circuit, and an amount of HL solution sufficient to flush substantially all of the animals blood (for the 7 kg baboon approximately 2 liters of solution) was allowed to blood-substitute the animal, and whole and diluted blood was removed as venous effluent and saved for revival. Following this, its heart was arrested by the intra-arterial administration of 15 ml 2M KCl added via the secondary heat exchanger.

After the heart was arrested, the solution indicated below designated HLB was added to the reservoir and circulated into the animal. As this solution perfused into the animal, a blood-blood plasma-substitute mixture was continuously removed as a venous effluent until the HLB solution replaced the initial circulating solution. The temperature was then dropped to 2° C. as rapidly as possible, while maintaining CVP and wedge pressures at acceptable values. Rewarming then began. During this period, HLB solution was periodically drained from the animal's circulation while adding new HLB solution to the perfusion apparatus.

The animal was warmed keeping the CVP below 5 mm Hg. When the esophageal temperature reached 15° C., the animal's own whole blood collected during cooling was added to the circuit, replacing the HLB solution. Following this, enough donor whole blood was added to raise the hematocrit above 20%.

Heartbeat resumed when the body temperature rose. As the temperature rose, the hematocrit was elevated until it reached between 25–35%. As the temperature climbed above 25° C. Lasix was injected iv. Over the next hour, the baboon was warmed. Ventilation was initiated, and the baboon's body temperature rose to 37° C. A dopamine iv drip was begun when body temperature reached 25° C. As the baboon was warmed further, the dopamine drip was increased, and then, as blood pressure climbed, it was reduced, and then discontinued. The animal was removed from bypass, the catheters and cannulas pulled, and incisions closed. Sodium bicarbonate was administered iv as needed to manage acidosis. The animal woke and was conscious.

The circulating fluid was sampled periodically from the right femoral artery and the pH, electrolyte levels and hematocrit were determined and are reported in Table I.

Solution Compositions (in mM concentrations except HES [g/l])

| Solution | HES | NaCl | MgCl$_2$ | CaCl$_2$ | Glucose | Na Lactate |
|---|---|---|---|---|---|---|
| HL | 60 | 115 | 0.25 | 2.5 | 5 | 28 |

HLB has the same composition as HL but includes in addition 5 mM NaHCO$_3$. HES is high molecular weight hydroxyethyl starch.

TABLE I

| Sample | time (min) | pH @ 37° C. | Total Calcium | K+ | HCT* |
|---|---|---|---|---|---|
| 1 | 0:00 | 7.654 | 9.3 | 3.1 | 40 |
| 2 | 0:15 | 7.646 | | | |
| 3 | 0:31 | 7.555 | | | |
| 4 | 0:58 | 7.536 | 8.9 | 2.7 | 39 |
| 5 | 1:13 | 7.627 | 8.9 | 3.2 | 25 |
| 6 | 1:40 | 7.340 | | < | <0.5 |
| 7 | 1:47 | 7.201 | | < | 0.5 |
| 8 | 1:56 | 7.455 | | 2.4 | 0.25 |
| 9 | 2:09 | 7.326 | | | 0.25 |
| 10 | 3:01 | 7.468 | 10.4 | 3.2 | |
| 11 | 3:53 | 7.498 | 10.5 | 2.9 | |
| 12 | 4:11 | 7.657 | 9.5 | 3.9 | 5.0 |
| 13 | 4:18 | 7.439 | 6.7 | 5.9 | 22 |
| 14 | 4:35 | 7.593 | 8.9 | 4.3 | 13 |
| 15 | 5:02 | 7.380 | 8.0 | 3.2 | 23 |
| 16 | 5:23 | 7.285 | 8.8 | 2.7 | 26 |
| 17 | 5:41 | 7.110 | 9.2 | 3.1 | 32 |
| 18 | 6:07 | | 9.0 | 4.4 | 36 |
| 19 | 6:11 | 7.038 | 7.8 | 3.8 | 34 |
| 20 | 6:32 | 7.284 | | 3.3 | 32 |
| 21 | 6:57 | 7.437 | | | |

*HCT = Hematocrit

EXAMPLE II

Reviving A Hamster After Ice-Cold Blood Substitution

In this experiment an 80 g female hamster was revived after chilling below 4° C. The animal was anesthetized by i.m. injection of ketamine and surrounded in crushed ice. When its body temperature reached 12°–16° C., it was removed from the ice and placed on a surgical stage. Its right femoral vein was cannulated with a modified 24 gauge angiocath, and its right femoral artery was cannulated with a micro-cannula.

The micro-cannula was attached to a line which was also connected to a reservoir and a pump, and the reservoir was chilled in crushed ice and contained ice-cold hypothermic blood substitute solution described in example I as HL. The animal was ventilated with 100% O$_2$ and perfused with 7 ml of blood substitute solution (150% of its estimated blood volume), until its hematocrit fell to 6%. Its heart was stopped with an iv injection of 0.15 ml of 1M KCl. During the perfusion, the blood substitute, whose initial pH was 5.5, comprised much of the venous effluent. The pH of the venous effluent first fell from 7.35 to 7.23, and then rose to 7.41, and later 7.55.

After 35 minutes of ice-cold blood substitution, perfusion was stopped and the animal maintained at the ice-point. After 30 minutes, whole blood was infused into the femoral artery, and blood substitute removed as a venous effluent.

The animal's heartbeat recovered after 25 minutes of blood substitution and the hematocrit reached 48% within another 10 minutes, and perfusion was halted. Five minutes later, breathing began. Within 20 minutes the animal was awake, and within one hour, it regained normal posture and was able to move about its cage. This recovery was the quickest ever observed using ice-cold blood substitution. The animal survived without complications for at least one week after the experiment and appeared normal.

The experiment confirmed the utility of the present formulation for use in ice-cold blood substitution. The solution containing sodium lactate initially has a pH of between 4 and 6, but after the lactate is metabolized, the resulting venous effluent has an alkaline pH, which can counteract acidity which may develop during rewarming. Also, there is some evidence accumulating that hypothermia can cause leakage of blood proteins out of the circulation, and into tissue, creating edema. The new formulation contains high molecular weight hydroxyethyl starch which has an average molecular weight of 480,000, and is therefore less likely to leak out of the vasculature than albumin, found in blood, or dextran 40.

EXAMPLE III

HL solution As An Artificial Plasma

A 80 g female hamster was injected im with an anesthetic mixture of ketamine, xylazine and acepromazine, and its right femoral artery and vein cannulated. Its blood was replaced with 4.8 ml of a formulation of the solution designated HL in Example I containing however 2 mM K+, until its femoral venous blood had a hematocrit of 18%. An equal amount of venous effluent was removed as the artificial plasma solution was infused into the femoral artery.

The catheters were removed and the incisions closed. The animal recovered from the anesthesia and survives at this writing, one week after the experiment. Since the initial hematocrit was 48%, dilution of the blood to 18/48 of its initial concentration represents a blood substitution of 62.5%.

EXAMPLE IV

Effect of Perfusate Composition on pH

Hamsters were injected i.m. with an anesthetic ketamine. After they were anethesized they were placed in crushed ice. When body temperature cooled to about 12° C. as measured by a rectal thermocouple, the hamsters were placed on a surgical stage. The carotid artery and jugular vein were exposed and cannulas were inserted into each. Body temperature was lowered further to below 5 degrees centigrade and using a peristaltic pump perfusate was pumped into the artery at about 0.3 ml per minute while venous effluent was collected and the pH of the effluent solution measured.

The perfusate solution consisted of the following constituents:

| | |
|---|---|
| High molecular weight hydroxyethyl starch- | 0.06 grams/ml |
| Sodium chloride | 115 mM |
| Magnesium chloride | 0.25 mM |
| Calcium chloride | 2.5 mM |
| Glucose | 5 mM |

A) Using the perfusate indicated above including 28 mM sodium lactate, having an initial pH 6.0 at room temperature (r.t.), the following pHs were obtained for samples of the effluent solutions:

| volume (ml) out | pH |
|---|---|
| 1 | 7.3 |
| 2 | 7.2 |
| 5 | 7.0 |
| 20 | 6.9 |

Effluent samples were then combined and the pH measured. The pH of the combined samples was 7.0.

B) Using the perfusate indicated above including Tris buffer (25 mM, having an initial pH 7.8 r.t., the following pHs were obtained for samples of the effluent solutions:

| volume (ml) out | pH |
|---|---|
| 1 | 7.3 |
| 2 | 7.25 |
| 4 | 7.28 |
| 8 | 7.3 |
| 11 | 7.16 |
| 20 | 7.2 |

Effluent samples were then combined and the pH measured. The pH of the combined samples was 7.2.

C) Using the perfusate indicated above including 28 mM sodium lactate and 10 mM sodium bicarbonate, having an initial pH 8.3 r.t., the following pHs were obtained for samples of the effluent solutions:

| volume (ml) out | pH |
|---|---|
| 1 | 7.3 |
| 2 | 7.2 |
| 5 | 7.32 |
| 8 | 7.41 |
| 12 | 7.53 |
| 20 | 7.55 |

Effluent samples were then combined and the pH measured. The pH of the combined samples was 7.5

D) Using the perfusate indicated above including 28 mM sodium lactate and 5 mM sodium bicarbonate, having an initial pH 8.2 r.t., the following pHs were obtained for samples of the effluent solutions:

| volume (ml) out | pH |
|---|---|
| 1 | 7.3 |
| 3 | 7.28 |
| 6 | 7.35 |
| 8 | 7.33 |
| 10 | 7.38 |
| 12 | 7.50 |
| 15 | 7.53 |
| 20 | 7.51 |

Effluent samples were then combined and the pH measured. The pH of the combined samples was 7.5

E) Using 2 solution system in which the solutions had the following compositions:

1) the perfusate indicated above including 28 mM sodium lactate having an initial pH 6.0 at room temperature; and 2) the perfusate indicated above including 28 mM sodium lactate and 5 mM sodium bicarbonate, having an initial pH 8.2 at room temperature.

The following pHs were obtained for the samples of the effluent solutions:

| volume out | pH |
|---|---|
| With 1: | |
| 1 | 7.25 |
| 4 | 7.13 |
| 8 | 7.11 |
| Switch to 2: | |
| 10 | 7.41 |
| 14 | 7.44 |
| 17 | 7.45 |
| 20 | 7.49 |
| 23 | 7.4 |

Effluent samples of ml 10–23 were then combined and the pH measured. The pH of the combined sample was 7.41

This series of experiments show that the addition of only 5 mM sodium bicarbonate to the lactate-buffered perfusate solution is sufficient to maintain near normal pH during total body washout at ice-cold temperatures. Interestingly and unexpectedly the lactate/bicarbonate buffer system is superior to biological buffers such as Tris when flushing animals with large volumes of solution at cold temperatures. Using the biologic buffers pH generally falls well below normal. Using only lactate the pH falls to an even lower pH (however use of lactate only when perfusing warm metabolically active animals, results in normal to basic pH). Using lactate with the addition of a small amount of bicarbonate, provided venous effluent with a near normal pH It was particularly surprising that such a small amount of bicarbonate added to the solution could maintain adequate pH of the venous effluent when perfusing large volumes.

EXAMPLE V

A Method For Replacing Blood With A Sterile Blood Substitute Solution

A patient experiencing intra-operative blood loss, or bleeding due to traumatic injury, is fitted with an iv line. A solution consisting of HL, $D^7L$, $D^{40}L$, PL, $H3D^{40}3L$, $H3P3L$, $D^{70}3D^{40}3L$, $D^{70}3P3L$, AL, H3A3L, or $D^{70}3A3L$ and electrolytes as indicated below is infused until normal circulating blood volume is re-established. In this solution, H is high molecular weight HES, 60 g/l; H3 is highmolecular weight HES, 30 g/l; $D^{70}$ is dextran 70, 60 g/l; $D^{70}3$ is dextran 70, 30 g/l, $D^{40}$ is dextran 40, 60 g/l; $D^{40}3$ is dextran 40, 30 g/l; P is low molecular weight HES also called pentastarch, 60 g/l; and A is human albumin (pasteurized) at 60 g/l . Mixtures, such as $H3D^{40}3$, denote starch mixtures, in which both HES and dextrans, either dextran 70 or 40, are present at 30 g/l (or 3 g/dl) each, or starch and albumin mixtures in which each component is present in this same 3:3 proportion. L is sodium lactate at 28 mM. If sodium bicarbonate (B) is used it is present at 5 mM.

Other combinations, such as 2:4 ratios of high molecular weight starch, such as high molecular weight HES, or Dextran 70; to low molecular weight starch, such as dextran 40 or low molecular weight HES (pentastarch); or low molecular weight protein such as albumin, can also be used. Alternatively, for some uses, especially when the use of the blood substitute solution is temporary, a lower concentration of starch or albumin, such as 30–40 g/l, may be utilized.

The remaining components including electrolytes, aside from the starch or albumin, are as follows (in mM):

NaCL 110–120, KCl 3, $MgCl_2$ 0.45, $CaCl_2$ 2.5, glucose 5–10, sodium lactate 28. These concentrations will be preferred particularly when the subject has suffered both blood volume loss and significant tissue trauma.

Therefore, HL solution will have the above components, plus 60 g/l hetastarch.

In some uses of this solution, where tissue damage is not expected or is not significant, $MgCl_2$ may be 0.5–1.5 mM, glucose may be 5 mM and KCl may be 4–5 mM.

In this example, a person transfused with HL solution might receive a dose of amylase in an amount capable of digesting 20 g of hetastarch per liter of blood per day. Thereby, if during an infusion of HL solution, 50 grams of hetastarch were infused per each liter of a patient's blood during a rescue situation or in response to serious intraoperative bleeding, the iv introduction of amylase in the above quantity would reduce the hetastarch to only 30 g/l on the first day, and 10 g/l after the second day. However, the actual amount of hetastarch would decrease even faster than that, since a portion of the hetastarch is cleared even without digestion by the added amylase.

It may be necessary to monitor plasma protein as well as starch, otherwise the patient may be left with too little plasma oncotic pressure. It may also be necessary to use an amylase inhibitor if too much amylase has been added. It may also be necessary to monitor blood glucose levels to prevent these from climbing too high during the digestion of the starch. If the glucose concentration climbs too quickly, it can be lowered by dialysis or by administration of insulin.

In order to digest dextran 70, a glycosidase enzyme which breaks 1,6 alpha glucosidic linkages may be employed, with or without amylase. Amylase may be most active on hetastarch and pentastarch, since these starches contain mostly 1,4 alpha glucose linkages. However, the hydroxyethyl forms of these starches might be resistant to amylase digestion.

Alternatively, starch may be removed through the extracorporeal use of beads or other fixed surfaces, composed of or containing materials that actively bind starch.

EXAMPLE VI

A Method for Preserving Organs and Tissues for Transplantation

General Method and Utility

A mammalian organ donor is used in the present method. If the organ donor is human, the procedure is carried out on the cadaver after death has been determined preferably using the criteria of brain death. Respiratory and circulatory support may be continued in this case after death is pronounced. Cannulas, monitors, temperature and pressure probes and connections to the pump and reservoir for the solution to be administered to the subject are made essentially as described in Example I with appropriate modifications depending upon the species of the donor subject. The donor subject is is chilled and blood-substituted to a minimum deep esophageal temperature of 2° C. After reaching that temperature, vital organs such as the kidney, liver, heart, lung and pancreas, and tissues such as bone marrow, cornea, and eye lens are removed and reserved under appropriate storage and transport systems for eventual distribution to recipients. Following this, the cadaver is perfused with another blood substitute which contains freeze-protecting agents such as glycerol. Tissues, such as skin, bone, nerve, joints, and cartilage are then removed, and frozen to liquid nitrogen temperatures. These can then be thawed and used in surgical procedures.

In this perfusion procedure for preparation of cadaver tissues for freezing, other cold protecting agents, or combinations of cold protecting agents, can be used in place of glycerol, or in addition to glycerol. These include ethylene glycol, propylene glycol, dimethylsulfoxide (DMSO), urea, trimethylamine (TMA), trimethylamine oxide (TMAO), glucose, sucrose, sorbitol, and trehalose.

While HL and HLB are described below in the example, alternatively $D^{40}L$ or $D^{70}L$ may be substituted for HL, and $D^{40}LB$ or $D^{70}LB$ may be substituted for HLB. Other kinds of whole body perfusates can be used starting with the above solutions. Biological buffers, such as tris, can be used, as well as HEPES, MOPS, EPPS etc., in addition to the HL, $D^{40}L$, and the other listed starch solutions. When these buffers are used, they can be used in 25 mM quantities, replacing 12.5 mM of NaCl or 12.5 mM of sodium lactate. These solutions can be titrated with HCl to pH 7.8.

Aside from the utility of these blood substitute solutions in lowering body temperature through core cooling (blood cannot readily circulate at very cold temperatures), total body perfusion with blood substitutes may remove cells, such as lymphocytes, and other materials, such as circulating proteins and certain cellular elements of the blood platelets, which may stimulate rejection of the graft or which may lead to graft versus host disease. Grafts, thoroughly perfused may be less antigenic, and thus better tolerated, than organs and tissues with blood, containing its formed elements and proteins.

Procedure

The cadaver is fitted with an endotracheal tube, and ventilated with 100% $O_2$ (in the case of a heart-beating cadaver). The right femoral artery is catheterized to allow blood pressure monitoring. A wedge catheter is implanted in the pulmonary artery.

An extracorporeal circuit is constructed with a venous outflow reservoir, a pump head, and a hollow fiber membrane oxygenator with an integral heat exchanger, flow meter and a secondary in-line heat exchanger added as close to the organ donor as possible. The circuit incorporates a section between the outflow cannula and the venous reservoir to remove effluent and a funnel/reservoir to quickly refill the venous reservoir with a blood substitute. A cooler to supply the oxygenator's built-in heat exchanger and the secondary heat exchanger with circulating ice water is also provided. All tubing in contact with blood or blood substitute is sterile. The venous reservoir and circuit is filled with HLB (HLB solution is HL solution,as described above, to which 5 millimoles of sodium bicarbonate is added to each liter).

A catheter is placed in the left brachial vein to allow monitoring central venous pressure. Arterial blood gases, pH, and hematocrit are measured in each sample, and in some cases, electrolytes and enzymes as well.

A venous outflow cannula is placed in the left femoral vein. An arterial inflow cannula is placed in the left femoral artery. Alternatively, the left jugular vein and carotid artery are cannulated. Heparin and methylprednisolone are injected iv An esophageal tube fitted with a temperature probe is inserted for recording deep esophageal temperature. EKG leads are attached, and the cadaver is wrapped in a cooling blanket. Coolant is then circulated to surface cool the organ donor.

The cadaver is placed on bypass and rapidly cooled with both core and surface cooling. When the body temperature reaches 2° C., various vital visceral and thoracic organs, such as the heart, lungs, kidney liver and pancreas; and tissues such as cornea, eye lens and bone marrow, are removed and placed in crushed ice.(Alternatively, these latter three tissues could be left and frozen in the procedure described below in Example 7.) If the heart continues to beat at low temperatures, it may be quieted with an intra-arterial injection with 2M KCL. As each organ or tissue is removed, their connecting blood vessels remaining in the cadavar are ligated, so that perfusion of the cadaver with freeze-protecting solution can begin.

The organs and tissues can either be refrigerated at approximately 0° C., or perfused either continuously, or intermittently with oxygenated HLB solution. Oxygenation can be supplied using a membrane or bubble oxygenator, such as is used in neonatal or pediatric surgery.

After these organs and tissues are removed, the cadaver is perfused with an ice cold HLB solution containing glycerol 14% (v/v). More preferred is HLB containing 4% DMSO, 4% glycerol and 0.05M glucose. This modified HLB solution is added to the bypass circuit, and the solution which it replaces is drained as a venous effluent. The glycerolated solution is continually added to the reservoir until the concentration of glycerol in the peripheral venous circulation approaches that of the solution in the reservoir. At this time, the perfusate is recirculated until the concentration of glycerol no longer declines. If the concentration of glycerol (or other cold protecting agent) falls, more glycerolated (or other cold protecting agent) solution is added to the reservoir, while a similar amount of venous effluent is removed. Generally, about 70 liters of glycerolated HLB solution would be used in the preservation of a 70 kg cadaver.

After the cadaver is thoroughly perfused with cold-protecting agents, various tissues, such as skin, bone, cartilage, muscle, nerve, joints and whole limbs, are harvested, and then frozen at progressively lower temperatures. These tissues are placed in plastic containers, and chilled first to $-40°$ C., then to $-79°$ C., and then to $-196°$ C. The tissues can be stored indefinitely at $-196°$ C. prior to use. When used, the tissues are thawed in ice-cold water, or warmed by microwave or diathermy. After thawing, the tissues are stored in HLB solution prior to surgical replantation.

Alternative protocols may be used. These may include freezing first to $-79°$ C., and then to $-196°$ C.

EXAMPLE VII

A Method for Ice-Cold Neurosurgery and Cardiovascular Surgery

The patient is fitted with an endotracheal tube, and ventilated with 100% $O_2$. Anesthetic is maintained either by iv infusion (such as is used with pentothal,) or with gaseous anesthesia (such as flether). The right femoral artery is catheterized to allow blood pressure monitoring. Optionally, a wedge catheter is used to measure pulmonary arterial pressure.

An extracorporeal circuit is constructed with a venous reservoir, a pump head, and a hollow fiber membrane oxygenator and with an integral heat exchanger, flow meter and a secondary in-line heat exchanger added as close to the patient as possible. The circuit incorporates a section between the outflow cannula and the venous reservoir to remove effluent and a funnel/reservoir to quickly refill the venous reservoir with a blood substitute. A cooler to supply the oxygenator's built-in heat exchanger and the secondary heat exchanger with circulating ice water is also provided. All tubing in contact with blood or blood substitute is sterile. The venous reservoir and circuit is filled with HL solution.

A catheter is placed in the left brachial vein to allow monitoring central venous pressure. Arterial blood gases, pH, and hematocrit are measured in each sample, and in some cases, electrolytes and enzymes as well.

Venous outflow cannulas are placed in the femoral veins bilaterally, or in only the left femoral vein. An arterial inflow cannula is placed in the left femoral artery. Heparin and methylprednisolone are injected iv. An esophageal tube fitted with a temperature probe is inserted for recording deep esophageal temperature. EKG leads are attached, and the patient is wrapped in a cooling blanket. Coolant is then circulated to surface cool the patient.

The patient is placed on bypass and rapidly cooled with both core and surface cooling. When deep body temperature reaches 25° C., the HL solution is drained, while it is replaced isovolemically with ice-cold HLB solution (as noted above, HLB solution is HL solution to which 5 millimoles of sodium bicarbonate is added to each liter of HLB). When the body temperature reaches between 12° C. and 2° C., various neurosurgical operations can be performed.

Generally, if long periods of standstill are required, temperatures near the ice-point may be preferred.

Alternatively, L solution can be used as a bypass prime in the place of HL in the period of initial administration to wash the blood out of the circuit. In an alternative, though less preferred method, Plasmalyte, Ringer's solution or Ringer's lactate, Normasol, 0.9 saline or another such crystalloid compound solution may be used for this purpose. On warming, the L solution or other crystalloid solution can by perfused through the bypass circuit to remove the starch-containing solution, prior to the introduction of the blood-crystalloid solution used earlier to remove blood. Optionally, mannitol or an other metabolically inactive sugar can be added to the crystalloid solution to a concentration of 6 to 6.5 g/l to provide oncotic pressure.

As described above, starch digesting enzymes can be used in this procedure. Also in some embodiments, KCl concentration can be 4-5 mM, $MgCl_2$ concentration can be 0.5-1.5 mM when either HL or HLB solution is administered, particularly where extensive tissue trauma is not expected.

EXAMPLE VIII

A method for Isolated Regional Perfusion of Chemotherapeutic Agents in Ice Cold Blood Substituted Patients with Vital Organ Cancer In this example isolated regional perfusion of a subject having cancer in a vital organ is used to facilitate the administration of intense doses of chemotherapeutic agents to organs or tissues carrying malignant tumors. By isolating the circulation of the chemotherapeutic agent to the approximate site of tumor location, the systemic side effects of intense high dose chemotherapy, such as myelosuppression, nephrotoxicity, alopecia, pulmonary fibrosis, or cardiotoxicity can be substantially reduced or avoided.

The patient's body temperature is brought close to the ice point (1°-7° C.) as in the above example, and the blood pump is stopped. The organ where the malignant tumor is located, such as the liver, is infused with warmed oxygenated blood or the plasma-like solution of the invention such as HLB, through an artery supplying the organ—in this example the hepatic artery, and is removed as a venous effluent—in this example the hepatic vein. The infusion fluid will also contain high doses of chemotherapeutic anti-neoplastic drugs, such as doxorubicin, mitomycin, cisplatinum or the like. The dose of the drug circulated to the organ using this method may be higher than the dose ordinarily recommended for iv administration to a patient, for example in a range of 1.5 to 50 times that ordinarily administered on the basis of the effective concentration of drug in the circulating fluid.

As all of the other blood vessels leading to and from the perfused organ are cross clamped, the other organs are not exposed to the chemotherapeutic drug, thereby protecting untreated normal tissues that ordinarily have a high mitotic index or rate of cell division such as bone marrow, the gastro-intestinal mucosa, skin and hair. In addition since the treated organ is eventually flushed of the chemotherapeutic agent using this procedure, toxicity to the kidney is lower since the amount of chemotherapeutic agent excreted through the kidney is lower.

Additionally the treated organ or area can be externally warmed by light, infra-red lamps, diathermy or other means, in addition to core warming, to a temperature at with the tumor cells (and not normal cells removed from the area of regional perfusion) actively and selectively accumulate the toxic drug which will then lead to the death of these malignant cells.

Following exposure of the afflicted organ or area to warmed oxygenated blood or blood substitute carrying high concentration of anti-cancer drugs, the organ is then cooled by the circulation of ice-cold plasma like substance, which flushes out the blood or circulating solution containing the cytotoxic drugs. After completely flushing the organ, the cross clamps are removed, and the whole body is then perfused with more of the plasma-like substance, such as HLB or other blood substitute solution to flush out any remaining toxic anti-cancer agent. Following this perfusion of the general circulation, blood is then reintroduced in the manner described in the previous examples. The patients own blood may be used or the patient may be completely transfused with donor blood.

The patient is warmed to normal body temperature for its species and revived.

EXAMPLE IX

A Method for Removing Pathogens, Poisons and Toxins From Blood by Replacing Blood with a Sterile Plasma-like Solution A patient suffering from severe blood-born viremia, such as HIV or hepatitis, fungal infection or bacterial disease, or from heavy metal exposure, toxins organic poisons or other etiologic agent is fitted with iv catheters in both radial veins.

A solution consisting of HL, $D^{70}L$, $D^{40}L$, PL, $H3D^{40}3L$, H3P3L, $D^{70}3D^{40}3L$ $D^{70}3P3L$, AL, H3A3L, or $D^{70}3A3L$ and electrolytes as indicated below is infused while blood is collected as a sterile venous effluent. In this example each oft he components of the above-indicated solutions is as specified in Example 5.

Other combinations, such as 2:4 ratios of high molecular weight starch, such as high molecular weight hetastarch, or Dextran 70; to low molecular weight starch, such as dextran 40 or pentastarch; or low molecular weight protein such as albumin, can also be used. Alternatively, for some uses, especially when the use of the blood substitute solution is temporary, a lower concentration of starch or albumin, such as 30-40 g/l, may be utilized.

The remaining components including electrolytes, aside from the starch or albumin, are as follows (in mM):

NaCl 110-120, KCl 3, $MgCl_2$ 0.45, $CaCl_2$ 2.5, glucose 5-10, sodium lactate 28. These concentrations will be preferred particularly when the subject has suffered both blood volume loss and significant tissue trauma.

In some uses of this solution, where tissue damage is not expected, $MgCl_2$ may be 0.5–1.5 mM, glucose may be 5 mM and KCl may be 4–5 mM.

Blood substitution and venous effluent collection is continued until the hematocrit is reduced to 10–15 percent (normal is 38–45 percent in mammalian primates and human beings). The patient is maintained on oxygen during this process. The effluent is centrifuged and the red cells (without the white cell layer) are removed and resuspended in sterile crystalloid solution such as plasmalyte and centrifuged again. The red cells are drawn off and rinsed repeatedly until the pathogen titer or concentration of toxins are reduced to insignificant levels. The red cells are resuspended in the plasma-like substance according to the invention and this then is infused while an equal volume of venous effluent is drawn off, and the red cells removed and rinsed as before.

This technique is repeated until concentrations of pathogen, toxin or poison fall below significant levels. At this time, any remaining red cells not infused are rinsed in crystalloid solution and reinfused in sterile crystalloid, to enable the hematocrit to return to normal. Alternatively, fresh transfused blood from uncompromised donors can be used in a final infusion to replace a portion of the blood cells bearing plasma-like substance, the portion infused having enough formed elements and blood components to permit adequate physiological activities such as blood clotting and carrier protein functions, until enough host blood can be regenerated.

In another embodiment transfused blood can be used to replace the blood substitute following the initial blood substitution. In still another embodiment, the patient can be chilled to a temperature below normal (1°–30° C.), and blood substituted until the concentrations of pathogen, toxin or poison fall below significant levels. Red cells resuspended in blood substitute, whole donor blood or some combination of the two can be infused following total body washout, and the patient can be warmed and revived.

Where HIV is involved, patients may be treated with antiviral agents such as AZT, DDI, DDC or combination of these or other anti-viral agents following total body washout, to impede the return of a high viral burden.

EXAMPLE X

A Method For Preserving A Non-living Biological Subject At Cryogenic Temperatures A non-living subject is chilled and blood-substituted to a minimum deep esophageal temperature of 2° C. Following this, the subject is perfused with another blood substitute which contains freeze protecting agents.

The subject is fitted with an endotracheal tube, and may be ventilated with 100% oxygen. An extracorporeal circuit is constructed with a venous outflow reservoir, a pump head, and a hollow fiber membrane oxygenator and with an integral heat exchanger flow meter and a secondary in-line heat exchanger added as close to the subject as possible. The circuit incorporates a section between the outflow cannula and the venous reservoir to remove effluent and a funnel/ reservoir to quickly refill the venous reservoir with a blood substitute. A cooler to supply the oxygenator's built-in heat exchanger and a secondary heat exchanger with circulating ice water is also provided. All tubing in contact with blood or plasma-like substance is sterile. The venous reservoir and circuit is filled with HLB (as described above.)

In some embodiments of the method the plasma-like solution will include electrolytes, aside from the starch or albumin, supplied as follows (in mM):

NaCL 115, KCl 3, $MgCl_2$ 0.45, $CaCl_2$ 2.5, glucose 10, sodium lactate 28. In some uses of this solution, as described above, $MgCl_2$ may be 0.5–1.5 mM, glucose may be 5 mM and KCl may be 4–5 mM.

A catheter is placed in the left brachial vein to allow monitoring central venous pressure. Arterial blood gases, and hematocrit are measured in each sample, and in some cases, electrolytes and enzymes as well.

A venous outflow cannula is placed in the left femoral vein. An arterial inflow cannula is placed in the left femoral artery. Alternatively, the left jugular vein and carotid artery are cannulated. Heparin and methylprednisolone are injected iv. An esophageal tube fitted with a temperature probe is inserted for recording deep esophageal temperature. EKG leads are attached, and the cadaver is wrapped in a cooling blanket. Coolant is then circulated to surface cool the subject.

The subject is placed on bypass and rapidly cooled with both core and surface cooling. The subject is perfused with an ice cold HLB solution containing in addition, glycerol, made by adding a quantity of HLB solution (860 ml) to each 140 ml of glycerol, until one liter of volume is achieved. (Alternatively, 140 ml of glycerol is added to the quantity of other solutes comprising a liter of HLB solution and then an amount of sterile water is added to achieve a volume of one liter. In either case, it may be desirable to first synthesize the cold-protecting solution without sodium bicarbonate, and then heat sterilize it, with the sodium bicarbonate added immediately before use.) In a more preferred embodiment HLB solution containing in addition 4% DMSO, 4% glycerol and 0.05M glucose is used.

The glycerolated HLB solution is added to the bypass circuit, and the solution which it replaces is drained as a venous effluent. The glycerolated solution is continually added to the reservoir until the concentration of glycerol in the peripheral venous circulation approaches that of the solution in the reservoir. At this time, the perfusate is recirculated until the concentration of glycerol no longer declines. If the concentration of glycerol falls, more glycerolated solution is added to the reservoir, while a similar amount of venous effluent is removed. Generally, about 40 to 70 liters of glycerolated HLB solution would be used in the preservation of a 70 kg subject.

After the subject is thoroughly perfused with cold-protecting agents, it is placed in a plastic container, and chilled first to −40° C., then to −79° C., and then to −196° C. It can be stored indefinitely at −196° C. prior to rewarming.

Alternative protocols may be used. These may include freezing first to −79° C., and then to −196° C.

In this procedure, other cold protecting agents, or combinations of cold protecting agents, can be used in place of glycerol, or in addition to glycerol. These include ethylene glycol, propylene glycol, dimethylsulfoxide (DMSO), urea, trimethylamine (TMA), trimethylamine oxide (TMAO), glucose, sucrose, sorbitol, and trehalose.

Alternatively, $D^{40}L$ or $D^{70}L$ and $D^{40}LB$ or $D^{70}LB$ and $D^{40}B$ or $D^{70}L$ may be substituted for HL and HLB in the method described herein.

Other kinds of whole body perfusates can be used other than the above solutions. Biological buffers, such as tris, can be used, as well as HEPES, MOPS, EPPS etc. in addition to the HL, $D^{40}L$, and the other starch solutions. When these buffers are used, they can be used in 25 mM quantities, replacing 12.5 mM of NaCl. These solutions can be titrated with HCl to pH 7.8.

EXAMPLE XI

Effect of Artificial Plasma Solution On Blood Total Glucose In Dogs

Two dogs denied food and water overnight were approximately ⅔ blood substituted by intravenous infusion of HL solution and exsanguination of a corresponding volume of blood. Essentially equal volumes of fluid were administered and withdrawn from each animal over a 15 minute period. Two other dogs were blood substituted in the same manner except with with Hespan® (hetastarch or high molecular weight hydroxyethyl starch.) Blood glucose values in one dog treated with each solution was evaluated every 15 minutes for 3 hours. The following values in mg/dl were observed:

| Blood Glucose concentration (mg/dl) | | |
|---|---|---|
| Time (min) | HL treated | Hespan ® treated |
| 0 | 174 | 139 |
| 15 | 175 | 140 |
| 30 | 172 | 151 |
| 45 | 164 | 159 |
| 60 | 162 | 165 |
| 1:15 | 163 | 169 |
| 1:30 | 165 | 175 |
| 1:45 | 164 | 185 |
| 2:00 | 172 | 183 |
| 2:15 | 168 | 186 |
| 2:30 | 167 | 198 |
| 2:45 | 169 | 184 |
| 3:00 | 162 | 190 |

It was noted that glucose levels in the HL solution-treated animal were relatively constant and were never more than 6–7 mg/dl from the midpoint value of 167 mg/dl in the HL treated dog. In the Hespan® treated animal, values of blood glucose vary widely, as much as 29–30 mg from the midpoint value of 168 mg/dl. The HL treated animal thus appeared to maintain circulating glucose levels better than the Hespan® treated animal.

EXAMPLE XII

Effect of Artificial Plasma Solution On Platelets In Dogs

Four dogs were treated in the same manner as described in Example 11, two with HL solution and two with Hespan®. Platelets counts were also evaluated in each blood sample taken from each dog. The following are the results of platelet counts as a percentage of baseline (measured prior to substitution), from each dog, and then the average of 2 dogs treated with each solution (in parentheses):

| Platelet Counts (% of baseline) | | | | | | |
|---|---|---|---|---|---|---|
| Time (min) | Hespan ® treated | | | HL treated | | |
| 0 | 100 | 100 | (100) | 100 | 100 | (100) |
| 15 | 41.0 | 23.0 | (32.0) | 54.2 | 29.9 | (42.1) |
| 30 | 38.6 | 22.6 | (30.6) | 45.1 | 33.3 | (39.2) |
| 45 | 34.6 | 23.8 | (29.2) | 57.6 | 44.7 | (51.2) |
| 60 | 41.9 | 28.9 | (35.4) | 66.0 | 47.7 | (56.9) |
| 1:15 | 48.0 | 21.3 | (34.7) | 70.8 | — | — |
| 1:30 | 47.6 | 20.0 | (33.8) | 77.8 | 53.0 | (65.4) |
| 1:45 | — | 24.2 | — | — | 54.5 | — |
| 2:00 | 45.5 | 21.7 | (33.6) | 70.8 | 54.5 | (62.7) |
| 2:15 | 50.4 | 27.2 | (38.8) | 83.3 | 54.9 | (69.1) |
| 2:30 | 46.7 | 21.7 | (34.2) | 69.4 | 56.8 | (63.1) |
| 2:45 | 39.4 | 22.1 | (30.8) | 90.9 | 59.8 | (73.4) |
| 3:00 | 42.3 | 35.7 | (39.1) | 98.6 | 56.8 | (77.4) |

Platelet counts appeared to increase through time period of measurement in the HL-treated animals while platelet counts in the Hespan®-treated group remained low and had a lower rate of increase. Clinically, the Hespan®-treated animals appeared to hemorrhage noticeably more than the HL-treated animals.

EXAMPLE XIII

HL Solution Stabilization of Serum Calcium and Glucose Levels

In this example 16 rats were blood substituted by intravenous infusion of HL solution and exsanguination until approximately 1.5 times the blood volume of the rat was administered as HL solution containing (in mM) NaCL 113, KCl 3, $MgCl_2$ 0.45, $CaCl_2$ 2.5, glucose 10, sodium lactate 28. Six rats were treated the same way except that they received a comparable volume of Hespan® solution (high molecular weight hydroxyethyl starch.) For each rat the last 3 ml of the exsanguination effluent was retained for determination of serum calcium, magnesium and glucose levels. The following values in mg/dl were observed:

| HL Solution | | | | |
|---|---|---|---|---|
| Animal # | Calcium | Magnesium | Glucose | Δ Glucose |
| 1 | 9.5 | 2.1 | 213 | −31 |
| 2 | 8.9 | 1.9 | 166 | −16 |
| 3 | 8.9 | 1.9 | 238 | +31 |
| 4 | 8.4 | 2.3 | 153 | −25 |
| 5 | 9.0 | 1.9 | 192 | +15 |
| 6 | 9.5 | 2.1 | 213 | +4 |
| 7 | 9.0 | 2.0 | 237 | −2 |
| 8 | 9.5 | 1.8 | 179 | +4 |
| 9 | 9.1 | 2.0 | 233 | +6 |
| 10 | 8.8 | 1.9 | 204 | +13 |
| 11 | 11.7 | 2.2 | 191 | +16 |
| 12 | 8.9 | 1.8 | 168 | −8 |
| 13 | 8.9 | 2.1 | 184 | −4 |
| 14 | 9.6 | 2.1 | 148 | −23 |
| 15 | 9.1 | 2.1 | 183 | −8 |
| Average | 9.25 | 1.99 | 193 | −0.8 |

| Hespan ® | | | | |
|---|---|---|---|---|
| Animal # | Calcium | Magnesium | Glucose | Δ Glucose |
| 1 | 6.6 | 1.6 | 296 | −26 |
| 2 | 6.8 | 1.6 | 297 | −13 |
| 3 | 7.3 | 1.9 | 107 | −46 |
| 4 | 7.3 | 1.7 | 157 | −22 |
| 5 | 7.7 | 1.7 | 144 | −27 |

| Animal # | Calcium | Hespan® Magnesium | Glucose | Δ Glucose |
|---|---|---|---|---|
| 6 | 7.3 | 1.8 | 187 | −17 |
| Average | 7.16 | 1.71 | 198 | −25.1 |

The results demonstrate that higher levels of serum calcium and magnesium are obtained with HL as compared to Hespan®. Furthermore, although average glucose levels were similar, the average change in glucose values from that measured initially for each animal prior to blood substitution compared to that obtained at the end of blood substitution with each solution show that glucose concentrations were relatively unchanged in the HL substituted rats, but were much lower in the Hespan®substituted rats.

EXAMPLE XIV

Effective Cryoprotective Solutions and Protocols

A hamster (50 g female) is anesthetized with 0.03 ml i.m. of ketamine (100 mg/ml) and covered with crushed ice until rectal temperature was about 12° C. The animal was then placed on a surgical platform under a stereomicroscope. The carotid artery and jugular vein were exposed. A microcannula was inserted into the carotid artery. The animal was ventilated with 100% $O_2$ and body temperature was further lowered toward the ice point. Perfusion with HLB containing (in mM) NaCL 113, KCl 3, $MgCl_2$ 0.45, $CaCl_2$ 2.5, glucose 10, sodium lactate 28 and sodium bicarbonate 5 was initiated after venous puncture at about 10° C. After perfusion of one blood volume (at a rate of about 0.3 ml/min) the cryoprotective solutions listed below were perfused at a rate of 0.3 ml/min until the heart stopped. Then perfusion rate is increased to 0.6 ml/min. The animal is placed in a jar and frozen to liquid nitrogen temperature in a stepwise fashion. Following storage for at least 6 hours at −196° C. and at least 24 hours below −78° C., the animal is thawed and reperfused with HLB containing (in mM) NaCL 113, KCl 3, $MgCl_2$ 0.45, $CaCl_2$ 2.5, glucose 10, sodium lactate 28 and india ink. The heart is excised and examined under a high powered stereomicroscope equipped with video attachments. Using each of the cryoprotective solutions listed below in the procedure described above, the heart muscle was observed to be highly active. This activity is indicated by rhythmical movement of the surface of regions of the heart tissue.

Cryoprotective solutions tested successfully using this procedure are as follows:

| Solution | HLB | KCl | DMSO | Glycerol | Ethylene Glycol | FM* | PPdiol** |
|---|---|---|---|---|---|---|---|
| A | + | 10 mM | 2.5% | 2.5% | 2.5% | — | — |
| B | + | 10 mM | — | 1.4M | — | — | — |
| C | + | 3 mM | 0.75M | 0.75M | — | — | — |
| D | + | 3 mM | 5% | — | — | — | — |
| E | + | 10 mM | 5% | — | — | — | — |
| F | + | 3 mM | 5% | — | — | + | — |
| G | + | 3 mM | 0.5M | 0.5M | 1.0M | — | — |
| H | + | 3 mM | 10% | — | — | — | 10% |
| I | + | 3 mM | 4% | 4% | 0.05M | — | — |

*FM = formamide
**PPdiol = propanediol

It will be apparent from the forgoing that the blood plasma substitute solutions described herein may also be used to increase the circulating fluid volume of a hypovolemic subject. If used for this purpose, as described above, the concentration of the water soluble oncotic agent wherein the blood plasma substitute solution comprises a single oncotic agent will have the same concentration ranges as the plasma expander solutions. Thus for example when Dextran 40 or low molecular weight hydroxyethyl starch is used in the solution according to the invention its concentration is in a range of 6.0 to 8.5%. A solution comprising about 8% Dextran 40 (wt/v) or abut 80 grams (g) per liter (l) of water is generally used. When Dextran 70 or high molecular weight hydroxyethyl starch is used in the solution according to the invention its concentration is in a range of 5.5% to 6.5%. A solution comprising about 6% high molecular weight hydroxyethyl starch (wt/v) or about 60 grams (g) per liter (l) of water is generally used.

The new solutions according to the invention will be readily seen to confer several advantages over existing blood substitute solutions. Since the new formulation contains no biological buffer, no unphysiological components are present. All of the ingredients in the formula occur naturally in living mammals in significant quantities. Furthermore, the low pH of this formulation allows it to be terminally sterilized more readily. The components, being naturally occurring compounds omnipresent in significant quantities are inexpensive, and can therefore be produced at less cost. Since the formulation has a slightly acid pH, it has storage advantages as well.

We claim:

1. A method of preserving a non-living biological subject at cryogenic temperatures without the use of a solution comprising a biological buffer, said method comprising:

administering a first solution comprising an aqueous solution comprised of sodium lactate, and at least one water soluble oncotic agent selected from the group consisting of hydroxyethyl starch, dextran 40, dextran 70, and albumin, while lowering the temperature of said subject to about a temperature less than 10° C. and above ice point;

administering to said subject a second solution, comprised of sodium lactate, sodium bicarbonate, and at least one water soluble oncotic agent selected from the group consisting of hydroxyethyl starch, dextran 40, dextran 70, and albumin, and at least one cold protecting agent, in an amount to substantially remove said first solution; and further cooling said subject with the proviso that neither of said first or second solutions comprises a biological buffer.

2. The method of claim 1 wherein said first solution further comprises sodium bicarbonate.

3. The method according to claim 1, wherein at least one of said first and second solutions further comprises: NaCl about 110–120 mM, KCl about 3 mM, $MgCl_2$ about 0.45 mM, $CaCl_2$ about 2.5 mM, sodium lactate about 28 mM, and glucose in a range from about 5 mM to about 10 mM.

4. The method according to claim 1, wherein at least one of said first and second solutions further comprises:

NaCl about 110–120 mM, KCl from about 4–5 mM, $MgCl_2$ from about 0.5–1.5 mM, $CaCl_2$ about 2.5 mM, sodium lactate about 28 mM, and glucose about 5 mM.

5. The method according to claim 1, wherein said at least one cold protecting agent is selected from the group consisting of glycerol, ethylene glycol, propylene glycol, DMSO, urea, TMA, TMAO, glucose, sucrose, sorbitol and trehalose.

6. The method according to claim 5, wherein said at least one cold protecting agent is glycerol.

7. The method according to claim 6, wherein at least one of said first and second solutions comprises about 4% DMSO, 4% glycerol and 0.05M glucose.

8. A method of preserving a non-living biological subject at cryogenic temperatures without the use of a solution comprising a biological buffer, said method comprising:

administering a first solution comprising an aqueous solution comprised of sodium lactate, and at least one water soluble oncotic agent selected from the group consisting of hydroxyethyl starch, dextran 40, dextran 70, and albumin, while lowering the temperature of said subject to about a temperature less than 10° C. and above ice point;

administering to said subject a second solution, comprised of sodium lactate, sodium bicarbonate, and at least one water soluble oncotic agent selected from the group consisting of hydroxyethyl starch, dextran 40, dextran 70, and albumin, and, and at least one cold protecting agent selected from the group consisting of glycerol, ethylene glycol, propylene glycol, DMSO, urea, TMA, TMAO, glucose, sucrose, sorbitol and trehalose, in an amount to substantially remove said first solution;

wherein at least one of said first and second solutions further comprises NaCl about 110–120 mM, KCl from about 4–5 mM, $MgCl_2$ from about 0.5–1.5 mM, CaCl2 about 2.5 mM, sodium lactate about 28 mM, and glucose about 5 mM; and further cooling said subject;

with the proviso that neither said first or second solutions comprises a biological buffer.

9. The method according to claim 8 wherein said first solution further comprises sodium bicarbonate.

10. A method of preserving a non-living biological subject at cryogenic temperatures without the use of a solution comprising a biological buffer, said method comprising:

administering a first solution comprising an aqueous solution comprised of sodium lactate, and at least one water soluble oncotic agent selected from the group consisting of hydroxyethyl starch, dextran 40, dextran 70, and albumin, while lowering the temperature of said subject to about a temperature less than 10° C. and above ice point;

administering to said subject a second solution, comprised of sodium lactate, sodium bicarbonate, and at least one water soluble oncotic agent selected from the group consisting of hydroxyethyl starch, dextran 40, dextran 70, and albumin, and at least one cold protecting agent selected from the group consisting of glycerol, ethylene glycol, propylene glycol, DMSO, urea, TMA, TMAO, glucose, sucrose, sorbitol and trehalose, in an amount to substantially remove said first solution;

wherein at least one of said first and second solutions further comprises NaCl about 110–120 mM, KCl about 3 mM, $MgCl_2$ about 0.45 mM, $CaCl_2$ about 2.5 mM, sodium lactate about 28 mM, and glucose in a range from about 5 mM to about 10 mM; and further cooling said subject;

with the proviso that neither of said first or second solutions comprises a biological buffer.

11. The method according to claim 10 wherein said first solution further comprises sodium bicarbonate.

* * * * *